United States Patent
Itsuji

(10) Patent No.: US 9,134,182 B2
(45) Date of Patent: Sep. 15, 2015

(54) MEASUREMENT APPARATUS AND METHOD, TOMOGRAPHY APPARATUS AND METHOD

(71) Applicant: CANON KABUSHIKI KAISHA, Tokyo (JP)

(72) Inventor: Takeaki Itsuji, Hiratsuka (JP)

(73) Assignee: CANON KABUSHIKI KAISHA, Tokyo (JP)

(\*) Notice: Subject to any disclaimer, the term of this patent is extended or adjusted under 35 U.S.C. 154(b) by 98 days.

(21) Appl. No.: 13/894,065

(22) Filed: May 14, 2013

(65) Prior Publication Data
US 2013/0334421 A1     Dec. 19, 2013

(30) Foreign Application Priority Data
Jun. 14, 2012 (JP) .................. 2012-135260

(51) Int. Cl.
| | |
|---|---|
| *G01J 5/02* | (2006.01) |
| *G01N 21/55* | (2014.01) |
| *G01N 21/3581* | (2014.01) |
| *G01N 21/47* | (2006.01) |
| *G01J 3/42* | (2006.01) |

(52) U.S. Cl.
CPC ................. *G01J 5/0205* (2013.01); *G01J 3/42* (2013.01); *G01N 21/3581* (2013.01); *G01N 21/4795* (2013.01); *G01N 21/55* (2013.01)

(58) Field of Classification Search
CPC .................................................. G01N 21/3581
USPC ..................................................... 250/341.8
See application file for complete search history.

(56) References Cited

U.S. PATENT DOCUMENTS

| | | | |
|---|---|---|---|
| 5,489,984 A * | 2/1996 | Hariharan et al. | ............ 356/512 |
| 7,763,868 B2 | 7/2010 | Ouchi et al. | |
| 2012/0307258 A1* | 12/2012 | Koerner et al. | ............... 356/497 |

FOREIGN PATENT DOCUMENTS

JP         4046158         2/2008

\* cited by examiner

*Primary Examiner* — David Porta
*Assistant Examiner* — Hugh H Maupin
(74) *Attorney, Agent, or Firm* — Fitzpatrick, Cella, Harper & Scinto

(57) ABSTRACT

A measurement apparatus including a convergence unit for converging the electromagnetic wave to the object; a detection unit for detecting electromagnetic waves from the object; and an adjustment unit for adjusting a relative position between the object and the convergence position set by the convergence unit in a detecting region selected by using interval information about an interval between a first electromagnetic wave from the first reflecting surface and a second electromagnetic wave from the second reflecting surface, the first and second electromagnetic waves being acquired by using a detection result of the detection unit, in which the detecting region is a region in which a measurement position of the object at the time of detecting electromagnetic waves from the object is determined based on relative position information selected from and by using a plurality of pieces of information on the relative position corresponding to the interval information.

13 Claims, 16 Drawing Sheets

MEASUREMENT APPARATUS AND METHOD, TOMOGRAPHY APPARATUS AND METHOD

BACKGROUND OF THE INVENTION

1. Field of the Invention

The present invention relates to a measurement apparatus and a method each using an electromagnetic wave. The present inventions also relates to tomography apparatus and method.

2. Description of the Related Art

Terahertz waves are typically electromagnetic waves containing components within a frequency band between 0.03 THz and 30 THz. Many characteristic absorptions originated from structures and states of various substances, such as biomolecules, are seen in such a frequency band. By using the characteristic, an inspection technique to non-destructively analyze or identify substances has been developed. Also, application to a safer imaging technique using, instead of X-rays, and application to a high-speed communication technique have been proposed. Further, application to a tomography apparatus which visualizes inside of an object by using, for example, terahertz waves reflected by a refractive index interface inside the object, has been attracting an attention. By using this apparatus, it is expected that the structure inside the object can be visualized at the depth of about several 100 μm to about several 10 mm by taking advantage of the penetrating characteristic of terahertz waves.

Concerning the above-described techniques, Japanese Patent No. 4,046,158 discloses an example which measures thicknesses of an object based on a time interval between a plurality of terahertz wave pulses reflected by a plurality of interfaces of the object.

In the case of an apparatus which uses a time interval between a plurality of terahertz wave pulses, the accuracy of the measured time interval between the terahertz wave pulses is important. It has so far been considered that the time interval between terahertz wave pulses is greatly dependent on the interval between the interfaces of the object. However, according to the investigation of the present inventors, it is found that, in an apparatus configuration in which a terahertz wave pulse is collected and irradiated to an object, the time interval between terahertz wave pulses is also changed in dependence upon the position of the object arranged in the propagation path of the terahertz wave. Specifically, it was found that, for example, when one interface is located in a region in which the terahertz wave pulse propagates in a collimated manner (and which is also referred to as a collimated propagation region in this specification and which wave-optically corresponds to the depth of focus), and the other interface is located in the region in which the terahertz wave pulse is in a process of being collected (and which is also referred to as a collecting process region in this specification), a difference is caused between the optical paths along which the terahertz waves respectively propagate from the interfaces, and this difference in the optical paths is superimposed on the time interval.

Japanese Patent No. 4,046,158 does not show detailed descriptions cocnering an adjustment of the relative positional relationship of the plurality of interfaces of the object with respect to the optical system (also referred to as a convergence unit in this specification) for collecting a terahertz wave to the object. Therefore, a measurement result which is different from the interval between the actual interfaces may be output depending on the relative positional relationship between the object and the convergence unit. That is, the reliability of measurement accuracy may be lowered. Also, in a measurement method in which an electromagnetic wave irradiated to the object is continuous wave (CW), despite that a the used conception is not the same as described in Japanese Patent No. 4,046,158, the possibility of lowering the reliability of measurement accuracy can be pointed out.

SUMMARY OF THE INVENTION

A measurement apparatus according to an aspect of the present invention includes a convergence unit for converging the electromagnetic wave to the object; a detection unit for detecting electromagnetic waves from the object; and an adjustment unit for adjusting a relative position between the object and the convergence position set by the convergence unit in a detecting region selected by using interval information about an interval between a first electromagnetic wave from the first reflecting surface and a second electromagnetic wave from the second reflecting surface, the first and second electromagnetic waves being acquired by using a detection result of the detection unit, in which the detecting region is a region in which a measurement position of the object at the time of detecting electromagnetic waves from the object is determined based on relative position information selected from and by using a plurality of pieces of information on the relative position corresponding to the interval information.

According to the present invention, a detecting region in which measurement is performed is uniquely obtained by using the relative position between the object and the convergence position where an electromagnetic wave converged by the convergence unit, and by using the interval information about the interval between a plurality of electromagnetic waves respectively reflected by a plurality of reflecting portions of the object. Further, at the time of actually performing the measurement, the relative position is adjusted so that the portion of the object, which portion is to be measured, is included in the detecting region. Thereby, the positional relationship between the object and the convergence unit is stabilized, and hence the reliability of measurement accuracy is improved.

Further features of the present invention will become apparent from the following description of exemplary embodiments with reference to the attached drawings.

DESCRIPTION OF THE EMBODIMENTS

Figure 1A:
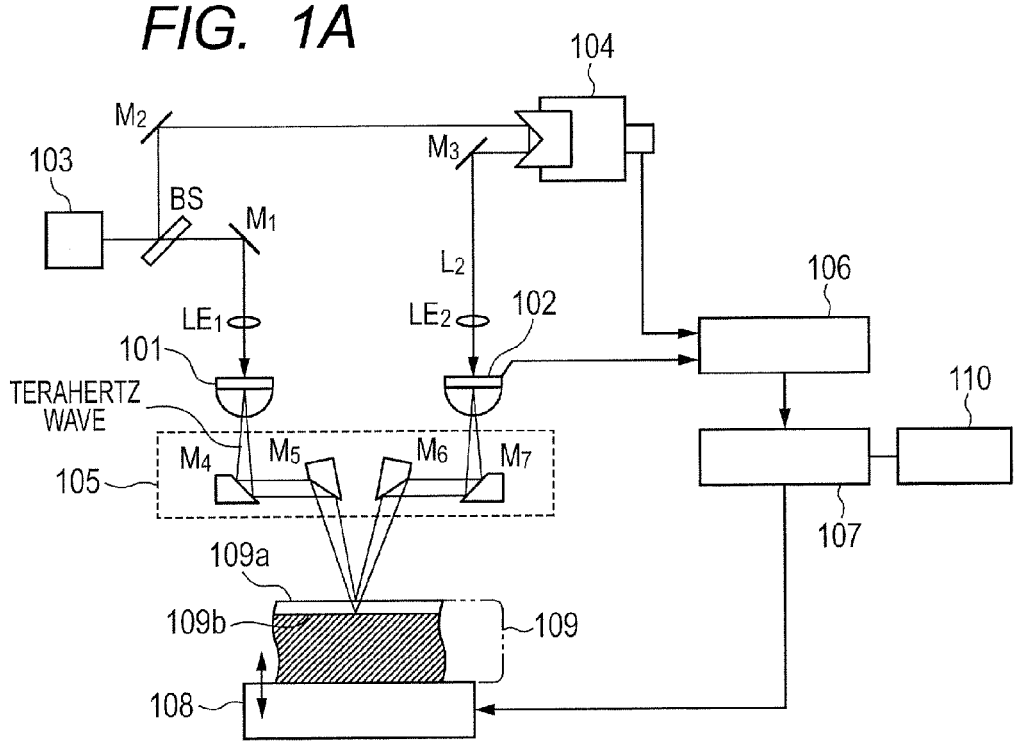
FIG. 1A and FIG. 1B are views each illustrating a schematic configuration of an apparatus of exemplary embodiment 1.

Exemplary embodiments of the present invention will now be described in detail in accordance with the accompanying drawings.

In the present invention, when each of the interfaces of the object exists in the collimated propagation region, the electromagnetic waves from the respective interfaces, such as terahertz wave pulses, propagate along the same optical path. As a result, the interval between the interfaces of the object can be reflected in the interval information of the electromagnetic waves, such as a time interval between terahertz wave pulses, from the plurality of interfaces. Therefore, it is important for the present invention that the reflecting portion and the interface of the object to be measured are stably adjusted in the collimated propagation region of the electromagnetic wave. The same can be said in cases where an electromagnetic wave other than a terahertz wave or a continuous wave which is not a pulse wave is used. In the case where a continuous wave is used, electromagnetic waves from the respective interfaces of the object are detected by using an interference technique which measures interference waves by moving a reference surface (such as a movable mirror), and the interval information about the distance between the interfaces is acquired from the correspondence relationship between the amount of movement of the reference surface and the detected intensity of the electromagnetic waves. In this case, the interval information is acquired at each of adjusted relative positions, and the relative positions is designated to be adjusted to a position at which the value of the interval information is stabilized.

The principle of the present invention will be described by taking, as an example, a form in which time waveforms of a plurality of electromagnetic wave pulses respectively reflected from reflecting portions of an object are acquired. In the present invention, the reliability of measurement accuracy can be improved in such a manner that the interfaces of the object to be measured are surely arranged in the collimated propagation region (wave-optically corresponding to the depth of focus) of an electromagnetic wave used for the measurement. In the present invention, a detecting region is set in the collimated propagation region of the electromagnetic wave, and the interfaces of the object are arranged in the detecting region. There is a case where the detecting region is the collimated propagation region itself, and also a case where the detecting region is a part of the collimated propagation region. For example, in the case where the object has a plurality of reflecting portions, such as a front surface, a rear surface, and a refractive index interface in the object, a plurality of electromagnetic wave pulses are detected from the object at the time when an electromagnetic wave pulse is irradiated to the object. At this time, the detecting region of the present invention is determined by monitoring the time interval between electromagnetic wave pulses resulting from the reflection at the plurality of reflecting portions of the object at the time when the plurality of reflecting portions are moved, for example, in a range from the collecting process region to the collimated propagation region. More specifically, a region in which the time interval between the electromagnetic wave pulses from the reflecting portions to be measured is not changed is defined as the detecting region. Further, by adjusting the relative position between the object and the convergence position set by the convergence unit, the interfaces of the object to be measured can be surely arranged in the detecting region included in the collimated propagation region of the electromagnetic wave used for the measurement.

The electromagnetic wave pulse used in the present invention may have a certain penetrating characteristic. Here, when the interval between the reflecting portions of the object is about several 100 μm to several 10 mm and when physical properties of the reflecting portions and physical properties of the region to the reflection portion are also to be acquired, a terahertz wave pulse can be preferably used. The terahertz wave pulse has an arbitrary frequency band in the range of 0.03 THz or more to 30 THz or less. Many characteristic absorptions originating from structures and states of various substances, such as biomolecules, are appeared in this frequency band. By applying the permeating characteristic and analyzing properties of the terahertz wave pulse, the apparatus and method of the present invention can acquire physical properties of as object as well as the information about the structure of the object.

Note that, as an exemplary technique in which an object is arranged in the collimated propagation region of an electromagnetic wave, there is known a microscope using a confocal optical system. The microscope using a confocal optical system is configured such that a signal from the focal point of the electromagnetic wave (corresponding to the collimated propagation region in this specification) is extracted by a pinhole or the like, and thereby the resolution in the depth direction is improved. In the microscope using a confocal optical system, a tomographic image is formed by moving the focal point in the depth direction of an object and detecting changes in the signal in association with the movement of the focal point. The present invention, however, is different from the microscope using the confocal optical system in that a tomographic image is formed by detecting a plurality of electromagnetic waves resulting from reflection caused in the inside of the collimated propagation region. In other words, in the technique of the microscope using the confocal optical system, signals from the collimated propagation region are averaged to be detected as a signal from one pixel, while, in the present invention, the collimated propagation region is divided into a plurality of pixels, and a signal of each of the pixels is detected. The electromagnetic wave used in the technique of the microscope using the confocal optical system is light near the visible region, and it has, for example, a wavelength which is smaller by several orders of magnitude than the wavelength of a terahertz wave. For this reason, the collimated propagation region defined in this specification is handled as almost a point therein. As a result, the microscope using the confocal optical system moves the focal point with respect to the inside of the object, and hence it does not have the concept that, as in the present invention, the object is moved in the collimated propagation region corresponding to the focal point. In the present invention, the internal structure of the object is measured in a detecting region included in the collimated propagation region, and hence the arrangement relationship about the object in the collimated propagation region is important. This importance does not exist in the technique of the microscope using the conventional confocal optical system. In the above-described points, the technique of the microscope using the confocal optical system is technically different from the spirit of the invention.

In the following, embodiments according to the present invention will be described in detail. Here, a time waveform acquisition apparatus and method, which acquire a time waveform of a terahertz wave pulse used as the electromagnetic wave, will be described as typical examples of the measurement apparatus and method. In particular, an apparatus and method, which accurately acquire terahertz wave pulses from an object having a plurality of reflecting interfaces, will be described by using a principle of an apparatus (THz-TDS apparatus, and THz-Time Domain Spectroscopy apparatus) that measures terahertz waves in the time domain.

(Exemplary Embodiment 1)

Exemplary embodiment 1, which can carry out the spirit of the present invention, will be described with reference to the accompanying drawings. FIG. 1A is a view illustrating a schematic configuration of an apparatus of exemplary embodiment 1. The present invention is described mainly based on the configuration illustrated in FIG. 1A, but configurations illustrated in FIG. 1B, FIG. 2A and FIG. 2B, as will be described below, can be used by being suitably combined with each other.

The apparatus at least includes, as portions configured to handle a terahertz wave pulse, the followings: a terahertz wave pulse generation unit 101 for irradiating a terahertz wave pulse to an object 109; a convergence unit 105 for converging, to the object 109, the terahertz wave pulse irradiated from the generation unit 101; and a detection unit 102 for detecting terahertz wave pulses from the object 109. In FIG. 1A, the convergence unit 105 is configured by four parabolic mirrors $M_4$ to $M_7$.

Further, the apparatus includes, as portions configured to acquire a time waveform of a terahertz wave pulse, at least the followings: a light source 103 configured to output excitation light for generation and detection of a terahertz wave pulse; a delay optical unit 104 configured to adjust the length of an optical path of excitation light $L_2$ propagating from the light source 103 to the detection unit 102; and a waveform acquisition unit 106 configured to acquire a time waveform of terahertz wave pulses from the object 109 by referring to a change in the optical path length of the delay optical unit 104 and an output (detection result) of the detection unit 102.

Further, in a terahertz wave pulse detecting region, the apparatus includes, as a portion by which an interface of an object to be measured is arranged, at least the following: an adjustment unit 108 for adjusting the relative position between the object 109 and the convergence unit 105 in the detecting region. By adjusting the position of the object 109 and/or the position of at least a part of the convergence unit 105, the adjustment unit 108 can adjust the relative position between the object and the convergence position set by the convergence unit 105. Further, the adjustment unit 108 adjusts the relative position between the object 109 and the convergence unit 105 in a detecting region which is selected by using time information about a time interval between a plurality of electromagnetic wave pulses from the object. This detecting region is a region where, when the electromagnetic wave pulses from the object are detected, the measurement position of the object is determined based on position information selected from and by using a plurality of pieces of position information of the object corresponding to the time information.

Figure 1B:
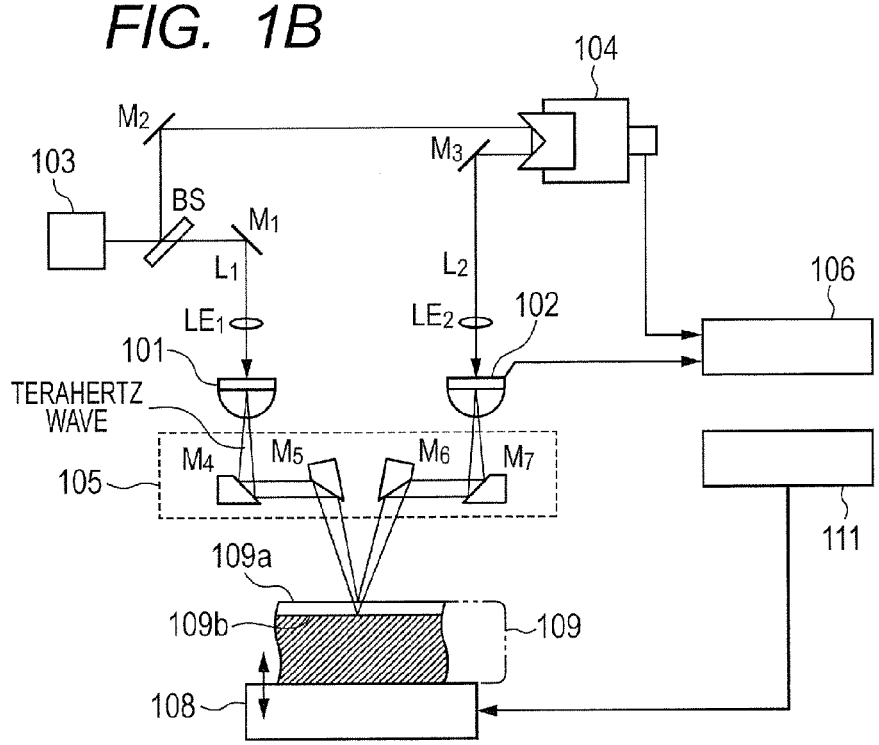

Further, the apparatus includes a region designation unit 107 configured to determine a detecting region by referring to a plurality of sets of time waveform information acquired by the waveform acquisition unit 106 at relative positions between the object 109 and the convergence unit 105. The region designation unit acquires a plurality of pieces of time information of the detected electromagnetic wave pulses and determines the detecting region from the plurality of pieces of time information. Further, the apparatus includes a memory 110 configured to store a plurality of sets of the relative position and the time waveform information acquired at the relative position. In some cases, the region designation unit 107 and the memory 110 are replaced, as illustrated in FIG. 1B, by a database 111 stored in a memory for storing beforehand the information about the detecting region. As the information about the detecting region, for example, a beam shape of a terahertz wave pulse is stored in correspondence with a relative position. Otherwise, a predetermined object 109 is assumed, and a plurality of sets of a relative position between the object 109 and the convergence unit 105 and time waveform information acquired by the waveform acquisition unit 106 at the relative position therefor can be stored in the database 111. In this way, the information used for specifying the detecting region of the apparatus is stored in the database 111.

With the time waveform acquisition apparatus and method configured as described above, the detecting region is determined according to a form of the object 109, by referring to the database 111 provided beforehand in the apparatus. Alternatively, after the object 109 is arranged, the detecting region is determined by measuring, at an arbitrary time, the relative position between the object 109 and the convergence unit 105, and information on a time interval between pulses from a plurality of reflecting portions of the object 109. Therefore, it is possible to easily perform measurement of the object 109 having various forms and properties, and hence the flexibility of the apparatus and method is improved.

The configuration of each of the units will be described in detail. Note that, for convenience of description, the present invention is described on the assumption that the object 109 has a first reflecting surface 109a and a second reflecting surface 109b. One of the two reflecting portions may be a reflecting portion on the surface of the object, of otherwise both the two reflecting portions may be in the inside of the object. Of course, the object may have two or more reflecting portions.

In FIG. 1A, a terahertz wave pulse can be generated in the generation unit 101 by using instantaneous current. For example, in a state where an electric field is applied to an element (also referred to as a photoconductive element in this specification) having an antenna pattern of a metallic electrode formed on a semiconductor thin film, excitation light is irradiated to the element, so as to generate a terahertz wave pulse. Otherwise, a PIN diode structure can be applied for generating a terahertz wave pulse. In the case where electro-optical effect of a nonlinear optical crystal is used, a terahertz wave can be generated also due to polarization which is caused in the crystal by irradiation of excitation light. Further, in the case where a semiconductor quantum well structure, or the like, is used, a method using the interband transition of carriers can also be applied. Any form of the generation unit 101 can be used as long as it can achieve the purpose of irradiating a terahertz wave pulse to the object 109.

In the detection unit 102, a change in the electric field intensity of a terahertz wave pulse can be detected by being converted into a change in current output from an element. For example, by use of a photoconductive element, a current corresponding to the electric field intensity of the terahertz wave pulse is detected based on a change in the photoconductivity of the element at the time when excitation light is irradiated to the element. In addition, it is also possible to use a method in which an electric field of a terahertz wave pulse is detected by using electro-optical effect, and also a method in which a magnetic field of a terahertz wave pulse is detected by using magneto-optical effect. When an electric field is detected by using electro-optical effect, a polarization splitter and an electro-optic crystal can be used. When a magnetic field is detected by using magneto optic effect, a polarization splitter and a magneto-optic crystal can be used. Any form of the detection unit 102 can be used as long as it can achieve the purpose of detecting the intensity of a terahertz wave pulse from the object 109 at the time when excitation light is irradiated to the object.

In the apparatus of FIG. 1A, the detection unit 102 is located at the position where the terahertz wave pulse reflected by the object 109 can be detected, but the arrangement of the detection unit 102 is not limited to this. As will be described below, it is only necessary to detect terahertz wave pulses from the first reflecting surface 109a and the second reflecting surface 109b of the object 109, and hence the detection unit 102 can also be arranged at a position where terahertz wave pulses transmitted through the object 109 can be detected. At this time, the detection unit 102 detects a terahertz wave pulse from each of the reflecting portions, which pulse is subjected to multiple reflection in the object 109.

The convergence unit 105 shapes the beam shape of the terahertz wave pulse generated in the generation unit 101, and converges the terahertz wave pulse to the object 109. Also, the convergence unit 105 makes the terahertz wave pulses from the object 109 incident on the detection unit 102. In the form of FIG. 1, the convergence unit 105 collects the terahertz wave pulse at one point on the object 109 by using the parabolic mirrors $M_4$ and $M_5$, and also collects the terahertz wave pulses from the object 109 by using the parabolic mirrors $M_6$ and $M_7$ so as to make the collected terahertz wave pulses incident on the detection unit 102. The form to converge the terahertz wave pulse is not limited to the form to collect light at one point, and, for example, the beam shape of the terahertz wave pulse may also be shaped into a strip shape, so as to be converged to the object 109. Here, an example using a parabolic mirror as means to converge the terahertz wave pulse is described, but a transmission type optical element, such as a lens, can also be used.

Figure 2A:
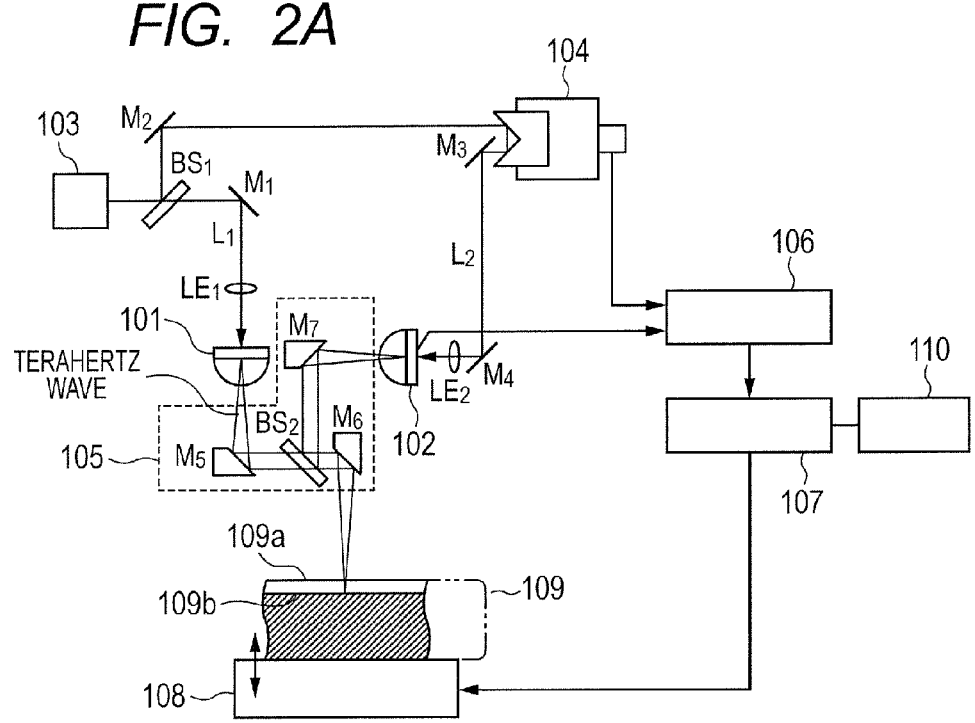
FIG. 2A and FIG. 2B are views describing a modification of the apparatus of exemplary embodiment 1.
Figure 2B:
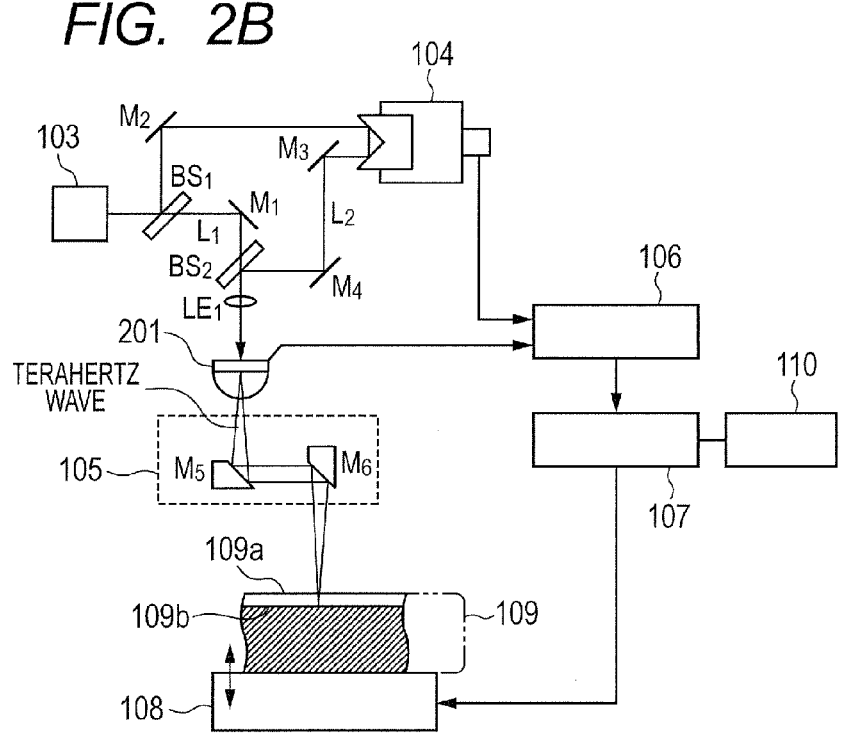

FIG. 2A and FIG. 2B are views each illustrating a schematic configuration of a time waveform acquisition apparatus including a modification of the convergence unit 105. In the apparatus of FIG. 2A, the convergence unit 105 is configured by parabolic mirrors $M_5$, $M_6$ and $M_7$ and a beam splitter $BS_2$. A terahertz wave pulse generated by the generation unit 101 is converged to the object 109 via the parabolic mirror $M_5$, the beam splitter $BS_2$ and the parabolic mirror $M_6$. The terahertz wave pulse reflected by the object 109 is made incident on the detection unit 102 via the parabolic mirror $M_6$, the beam splitter $BS_2$, and the parabolic mirror $M_7$. With this configuration, the terahertz wave pulse can be made incident substantially perpendicularly to the object 109. As a result, when an optical thickness is calculated from time waveforms of terahertz wave pulses from the respective reflecting portions, the apparatus can omit the optical length correction processing which is necessary at the time when a terahertz wave pulse is made incident obliquely to the object 109.

In the apparatus of FIG. 2B, the convergence unit 105 is configured by the parabolic mirror $M_5$ and $M_6$. A terahertz wave pulse generated by a generation/detection unit 201 is converged to the object 109 via the parabolic mirror $M_5$ and $M_6$. The terahertz wave pulse reflected by the object 109 is again made incident on the generation/detection unit 201 via the parabolic mirror $M_6$ and $M_5$. Here, the generation/detection unit 201 performs both generation and detection of a terahertz wave pulse. The generation/detection unit 201 is an integrated element of a portion for generating a terahertz wave pulse and a portion for detecting a terahertz wave pulse. It is desirable that the portions for generating and detecting a terahertz wave pulse are arranged at an interval not larger than the effective wavelength of the terahertz wave pulse made incident on the generation/detection unit 201. With such arrangement, it can be regarded that a terahertz wave pulse is generated and detected from and at the same place. Otherwise, a same element can perform both the generation and detection functions. For example, a configuration of a transceiver can be realized by using a photoconductive element. With such configuration, a terahertz wave pulse propagates along substantially the same optical path, and hence the space for passage of the terahertz wave pulse can be saved, so that the size of the apparatus can be expected to be reduced.

The light source 103 supplies excitation light to the generation unit 101 and the detection unit 102. In many cases, the light source 103 outputs ultrashort-pulsed laser light. The ultrashort-pulsed laser light output from the light source 103 has a pulse width of several 10 femtoseconds. In FIG. 1A, excitation light output from the light source 103 is branched by a beam splitter BS to $L_1$ (also referred to as pump light in this specification) and $L_2$ (also referred to as probe light in this specification). The pump light $L_1$ is made incident on the generation unit 101 through a mirror $M_1$ and a focusing lens $LE_1$. The pump light $L_1$ is used for generating of a terahertz wave pulse in the generation unit 101. The probe light $L_2$ is made incident on the detection unit 102 through a mirror $M_2$, the delay optical unit 104, the mirror $M_3$, and a focusing lens $LE_2$. The probe light $L_2$ is used as sample light for detecting a time waveform of a terahertz wave pulse in the detection unit 102. The wavelength of excitation light output from the light source 103 is changed by the drive wavelength of the generation unit 101 and the detection unit 102. A wavelength conversion element for changing the wavelength of the excitation light may also be provided, as required, in the middle of the propagation path of the pump light $L_1$ and the probe light $L_2$. Various characteristics, such as the wavelength and pulse width of excitation light output from the light source 103, and the laser repetition frequency, are suitably selected based on the specification required for the apparatus.

The delay optical unit 104 is a portion configured to adjust the optical path length difference between the pump light $L_1$ serving as excitation light, and the probe light $L_2$. In this exemplary embodiment, the time waveform of a terahertz wave pulse is acquired by using the principle of terahertz wave time-domain spectroscopy (THz—Time Domain Spectroscopy apparatus). In more detail, the apparatus measures a terahertz wave pulse by performing sampling with the probe light $L_2$ in such a manner that the output of the detection unit 102 is plotted each time when the optical path length difference between the pump light $L_1$ and the probe light $L_2$ is changed by a predetermined amount. The method for adjusting the optical path length in the delay optical unit 104 includes a method for directly adjusting the optical path length of the excitation light, and a method for adjusting the effective optical path length of the excitation light. The method for directly adjusting the optical path length of the excitation light includes a method that uses a folded optical system for folding the excitation light and a movable unit for moving the folded optical system in the direction in which the excitation light is folded. Otherwise, a rotatable optical system may also be applied as the movable unit. In this case, the folded optical system is moved along the direction of rotation of the movable unit. Otherwise, which two laser sources, in which the repetition frequency of each of the laser sources is changed, may be used as the light source 103, so as to respectively output the pump light $L_1$ and the probe light $L_2$. When the repetition frequency is different between the laser sources, the time difference between the pump light $L_1$ and the probe light $L_2$ is modulated, and the optical path length difference between the pump light $L_1$ and the probe light $L_2$ is converted based on the change in this time difference. The method for adjusting the effective optical path length includes a method for changing the time constant of the optical path length along which the excitation light propagates. As exemplified above, it is only necessary that the delay optical unit 104 is configured to be able to adjust optical path length difference between the pump light $L_1$ and the probe light $L_2$. In FIG. 1A, an example in which a folded optical system is used as the delay optical unit 104 is illustrated. However, more broadly speaking, it is only necessary that the delay unit is configured to adjust a difference between the generation time and the detection time of an electromagnetic wave, and it is not necessarily necessary that the delay unit is an optical unit.

Figure 3A:
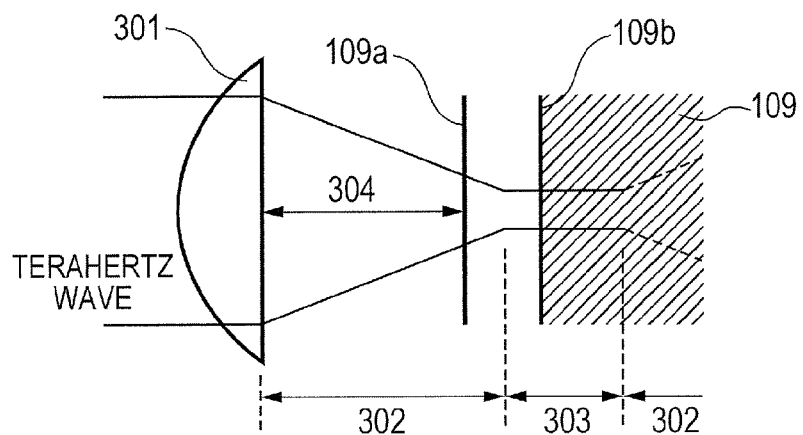
FIG. 3A, FIG. 3B and FIG. 3C are views describing a detecting region of the present invention and a method for obtaining the detecting region.
Figure 3B:
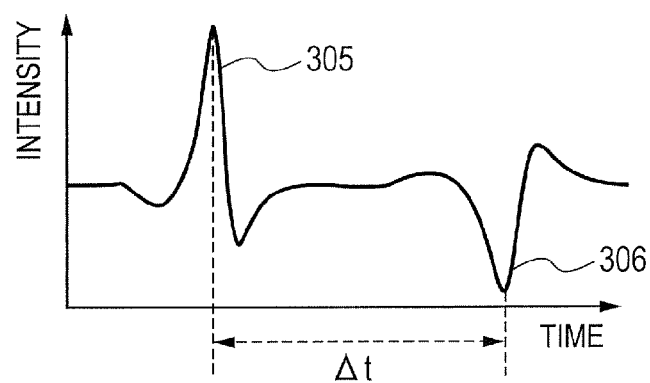

The waveform acquisition unit 106 is a portion which forms a time waveform of terahertz wave pulses from the object 109 by using the terahertz wave time-domain spectroscopy and by referring to the output of the detection unit 102, and the optical path length difference between the pump light $L_1$ and the probe light $L_2$, which difference being adjusted in the delay optical unit 104. When the object 109 has the first reflecting surface 109a and the second reflecting surface 109b, the time waveform formed by the waveform acquisition unit 106 includes at least, as shown in FIG. 3B, a primary pulse 305 from the first reflecting surface 109a, and a secondary pulse 306 from the second reflecting surface 109b. In FIG. 3B, the time interval Δt between the primary pulse 305 and the secondary pulse 306 is a value including at least the information on the optical length of the region sandwiched between the first reflecting surface 109a and the second reflecting surface 109b.

The adjustment unit 108 is a portion by which the relative position between the object 109 and the convergence unit 105 is adjusted to a detecting region. The apparatus of FIG. 1A is configured in a form in which the adjustment unit 108 is installed on the side of the object 109 to move the object 109, but the configuration of the apparatus is not limited to this. It is only necessary that the adjustment unit 108 is configured to enable the relative positional distance between the object 109 and the convergence unit 105 to be changed. Therefore, the adjustment unit 108 may otherwise be configured as a portion which moves the converging position of the terahertz wave pulse by integrally moving the generation unit 101, the detection unit 102, and the convergence unit 105. Otherwise, the adjustment unit 108 may be configured as a mechanism which adjusts the relative position between the object 109 and a part of the optical elements of the convergence unit 105. For example, in the case of FIG. 1A, by using the lens in the system for converging the terahertz wave pulse, the converging position of the terahertz wave pulse can be changed in relation to the position of the lens. The converging position of the terahertz wave pulse can be changed by adjusting the reflection angle of the mirror. In this specification, when a terahertz wave propagates through a focusing device 301 in FIG. 3A, the propagation beam shape of the terahertz wave is divided into a region which ranges from the focusing device 301 to the converging position of the terahertz wave (and which is referred to as a collecting process region 302 in this specification), and a region in which the converged terahertz wave propagates in a collimated manner (and which is referred to as a collimated propagation region 303 in this specification). The collimated propagation region 303 wave-optically corresponds to the depth of focus, and it can be regarded as a convergence position in the present invention. Here, the detecting region defined by the apparatus is a region in the collimated propagation region 303. In some cases, the detecting region is the same as the collimated propagation region 303. When, as in FIG. 3A, the first reflecting surface 109a and the second reflecting surface 109b of the object 109 are set as objects to be simultaneously observed, the detecting region is a region including at least the first reflecting surface 109a and the second reflecting surface 109b. since the detecting region is the same as the collimated propagation region 303 itself or included in the collimated propagation region 303, the first reflecting surface 109a and the second reflecting surface 109b can be included in the collimated propagation region 303. In FIG. 3A, the adjustment unit 108 adjusts a relative position 304 between the object 109 and the convergence unit 105 so that the first reflecting surface 109a and the second reflecting surface 109b are located within the detecting region in the collimated propagation region 303. Note that, in FIG. 3A, for convenience of description, the focusing device 301 for focusing the terahertz wave is described as a transmission type element. However, as in many examples of the present invention, it is possible to consider that the transmission type element can be replaced by a reflection type element.

Referring back to FIG. 1A, the region designation unit 107 is a portion which determines a detecting region of the apparatus. A detecting region is obtained by referring to a plurality of outputs from the adjustment unit 108 and the waveform acquisition unit 106. More specifically, a detecting region is obtained by referring to information on the relative position 304 obtained from the adjustment unit 108, and to time waveform information at the relative position, which information is obtained from the waveform acquisition unit 106. The time waveform information used for obtaining the detecting region is information on the time interval Δt between the primary pulse 305 and the secondary pulse 306 in FIG. 3B. The region designation unit 107 determines the collimated propagation region 303 by monitoring the region in which the value of time interval Δt is uniform with respect to a change in the relative position 304.

Figure 3C:
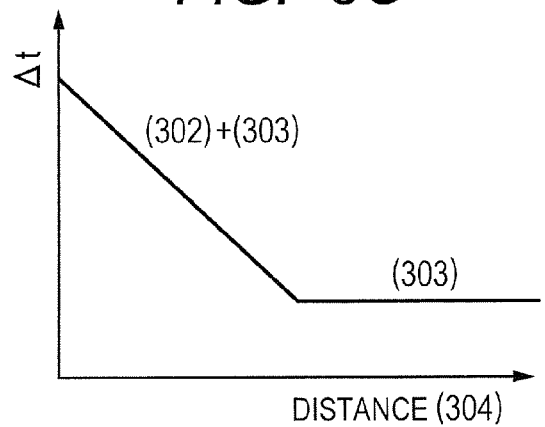

FIG. 3C illustrates in detail the operation of the region designation unit 107 described above. In FIG. 3C, the initial position of the relative position 304 is assumed to be a position illustrated in FIG. 3A. That is, the first reflecting surface 109a of the object 109 is in the collecting process region 302 of the terahertz wave pulse. The second reflecting surface 109b of the object 109 is in the collimated propagation region 303 of the terahertz wave pulse. In FIG. 3C, a state in which one reflecting portion to be observed is in the collecting process region 302, and in which the other reflecting portion is in the collimated propagation region 303 is represented as [(302)+(303)]. In FIG. 3C, a state in which both the reflecting portions are in the collimated propagation region 303 is represented as [(303)]. In FIG. 3C, when the relative position 304 is increased by using the adjustment unit 108, the first reflecting surface 109a is brought closer to the collimated propagation region 303. Then, the optical path difference between the terahertz wave pulses from the respective reflecting portions, which difference is described in the technical problem, is changed to be canceled. As a result, the time interval Δt between the primary pulse 305 and the secondary pulse 306 is reduced. When the relative position 304 (distance) is further increased so that the first reflecting surface 109a is included in the collimated propagation region 303, the time interval Δt is changed from the state [(302)+(303)] to the state [(303)]. That is, the value of the time interval Δt is fixed with respect to a change of the relative position 304. Note that the above description has been made on the assumption that the second reflecting surface 109b is always included in the collimated propagation region 303. When the relative position 304 is further increased in this state, the second reflecting surface 109b of the object 109 reaches the collecting process region 302 (region indicated by the dotted line in the propagation beam shape of the terahertz wave in FIG. 3A), and the time interval Δt is again increased. By such operations, the apparatus searches the collimated propagation region 303.

Thereafter, the apparatus sets the detecting region in the collimated propagation region 303, and stores the detecting region in correspondence with, for example, the relative position 304. As described above, the apparatus may also define the collimated propagation region 303 itself as the detecting region. Further, for example, the apparatus may define the detecting region inside the collimated propagation region 303 so as to leave a fixed amount of margin from the boundary of the collimated propagation region 303 or to leave a certain degree of margin with respect to the collimated propagation region 303. Since a terahertz wave has a long wavelength, the boundary between the collecting process region 302 and the collimated propagation region 303 may not be clear depending on the measurement accuracy of the apparatus. When the detecting region is defined in the collimated propagation region 303 so as to leave a margin with respect to the collimated propagation region 303, the unclearness of the boundary depending on the measurement accuracy can be avoided, so as to improve the robustness of the apparatus.

Referring back again to FIG. 1A, the memory 110 is a portion which stores the information on time interval Δt at each of the relative positions 304 described above. The region designation unit 107 defines a detecting region based on the information stored in the memory 110.

The process of determining a detecting region by using the region designation unit 107 and the memory 110 is performed in such a manner that, after the object 109 is arranged, the information on the relative position between the object 109 and the convergence unit 105, and the information on the time interval between the pulses from a plurality of reflecting portions of the object 109 are measured at an arbitrary time, and such that a detecting region is determined based on the measured information. In other words, a detecting region is determined by using the object 109 to be actually measured. For this reason, the apparatus and the method can easily perform the measurement of the objects 109 having various forms and properties, and hence the flexibility of the apparatus and the method can be improved. In the above-described apparatus or method, in order to determine a detecting region, there is used the information on the time interval between electromagnetic wave pulses at the time when the object 109 is relatively moved in the range from the collimated propagation region 303 to the collecting process region 304 in the propagation shape of an electromagnetic wave pulse. The position at which the time interval between electromagnetic wave pulses from the object 109 is changed can be confirmed by the moving object 109 relatively in this range. As a result, the detecting region can be specified, and the interface of the object, which interface is to be measured, can be stably adjusted to a region in the collimated propagation region of a terahertz wave.

In FIG. 1B, instead of the region designation unit 107 and the memory 110, the database 111 is used as a configuration of the portion for determining a detecting region. The information about the detecting region is stored beforehand in the database 111. The information stored in the database 111 includes, for example, information on time intervals between terahertz wave pulses measured beforehand by using a standard object specified by a measuring instrument. More particularly, it is desirable that the standard object specified by the measuring instrument is an object having an effective thickness substantially equivalent to the collimated propagation region 303 of a terahertz wave pulse. The apparatus beforehand measures a correspondence relationship between the relative position 304 and the time interval Δt by using this standard object, and the measurement result is stored as the information unique to the apparatus. In the case of a configuration in which the kind of the optical element used in the convergence unit 105 can be changed, the apparatus beforehand measures the correspondence relationship between the relative position 304 and the time interval Δt by using the standard object, and the measurement results are stored in a database. This information enables a user of the apparatus to specify the position of the collimated propagation region 303, and to set a detecting region in relation to the object 109.

Further, the database 111 may also be formed in consideration of the form of the object 109 (the size of the object, the position of the reflecting portion, and physical properties of the object, such as the refractive index and the distribution of the refractive index) so as to be used for adjusting the correspondence relationship between the relative position 304 and the time interval Δt. The correspondence relationship between the relative position 304 and the time interval Δt is measured by using, as standard objects, objects having various shapes and physical properties, and the measurement results are stored in the database 111. Then, the apparatus selects a standard object close to the form of the actual object 109 from the database 111, and obtains a detecting region by using the measurement result about the selected standard object. With this method, the form of the object 109 can be made close to the form of the standard object, and hence the measurement accuracy can be improved. Also when the correspondence relationship between the relative position 304 and the time interval Δt is adjusted according to the form of the object 109, since the amount of adjustment is small, the deviation in the measurement result between the standard object and the object 109 is reduced, so that the measurement accuracy of the apparatus can be easily maintained.

When the database 111 is used instead of the region designation unit 107 and the memory 110, the process of measuring the collimated propagation region 303 for each measurement is eliminated, and hence the operability can be improved. As a result, the flexibility of the apparatus and method can be improved.

An example of operation of the apparatus of the exemplary embodiment will be described based on the configuration of the apparatus of FIG. 1A. That is, the apparatus is configured to use the region designation unit 107 and the memory 110 as portions for determining a detecting region. The object 109 has at least the first reflecting surface 109a and the second reflecting surface 109b along the propagation path of a terahertz wave pulse. Here, for convenience of description, it is assumed that the object 109 has two reflecting portions of the first reflecting surface 109a and the second reflecting surface 109b.

Figure 6:
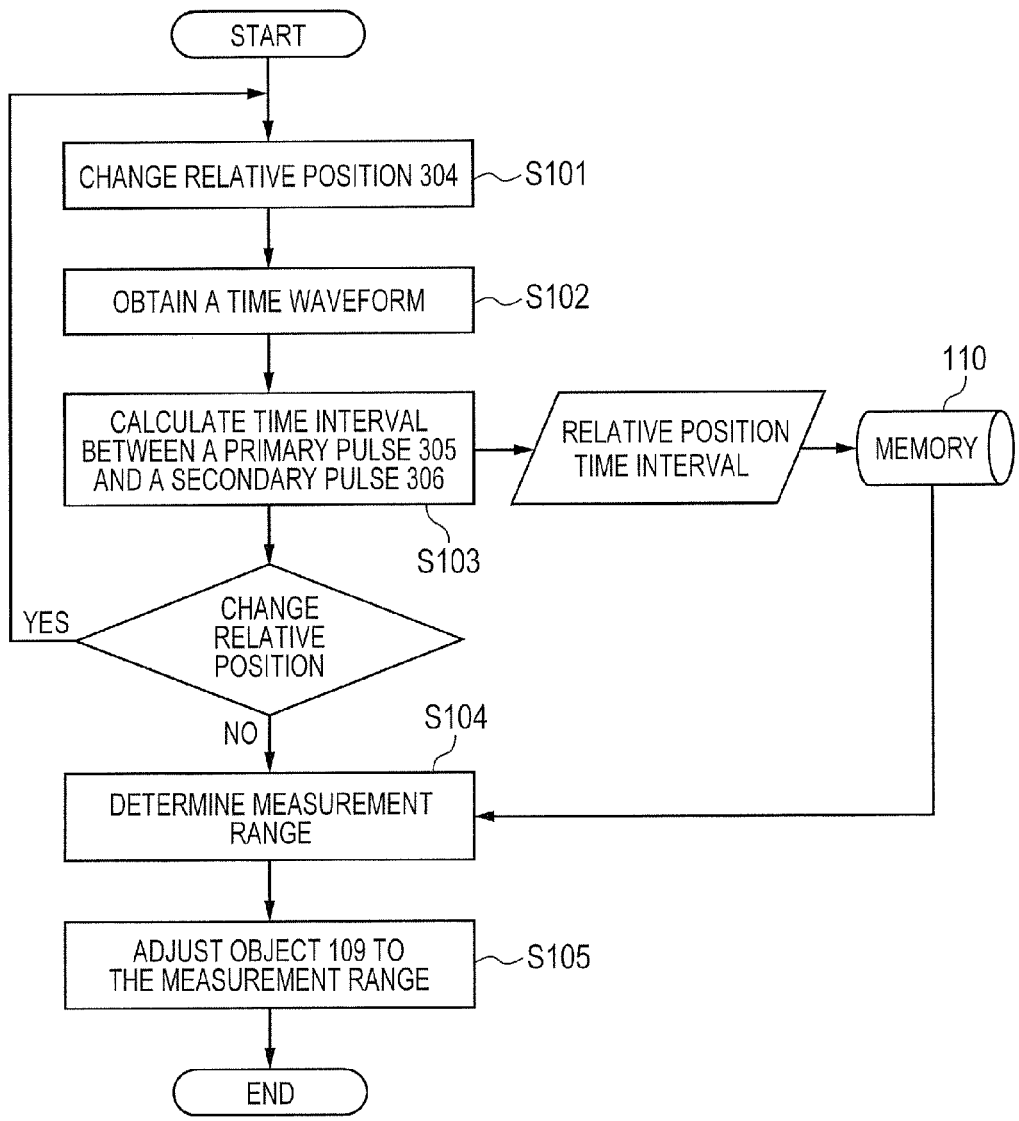
FIG. 6 is a flow chart describing a measurement method of the apparatus of exemplary embodiment 1.

FIG. 6 is a flow chart describing an operation flow of the apparatus of the exemplary embodiment. When the operation of the apparatus is started, the apparatus moves the relative position 304 between the object 109 and the convergence unit 105 by a predetermined amount by using the adjustment unit 108 (step S101). The amount of the movement of the relative position 304 depends on the measurement accuracy of the collimated propagation region 303. Otherwise, a form may also be adopted in which, only at the beginning of operation, the object 109 is moved to a predetermined position defined by a measurer, and in which, in the subsequent process, the object 109 is moved based on the predetermined position. The waveform acquisition unit 106 acquires a time waveform of terahertz wave pulses by using the principle of time domain spectroscopy and by referring to the output of the detection unit 102, and the optical path length difference between the pump light $L_1$ and the probe light $L_2$ caused in the delay optical unit 104 (step S102).

The time waveform of terahertz wave pulses acquired as described above includes the primary pulse 305 from the first reflecting surface 109a, and the secondary pulse 306 from the second reflecting surface 109b as shown in FIG. 3B. The region designation unit 107 calculates the time interval $\Delta t$ between the primary pulse 305 and the secondary pulse 306. The region designation unit 107 stores, in the memory 110, the relative position 304 and the time interval $\Delta t$ at the time of acquisition of the time waveform (step S103).

Here, when the condition for ending the movement of the relative position 304 is not satisfied, the process returns to step S101. The condition for ending the movement of the relative position 304 can be set as follows. For example, when the amount of movement of the relative position 304 in step S101 is defined, the number of repetitions from step S101 to step S103 is set beforehand, and the number of repetitions is set as the condition for ending the movement of the relative position 304. The direction of movement of the relative position 304 is set to the direction of uniformly increasing the relative position 304, or the direction of uniformly decreasing the relative position 304, or is set to a combination of these directions. The direction of movement of the relative position 304 is set by the measurer in view of the form of the object 109. In the case of this form of the apparatus, since the number of repetitions of the process from step S101 to step S103 is defined, the process is surely ended, and hence the operation can be easily stabilized. Further, in the case where the information on the relative position 304 and the time interval $\Delta t$, which are stored in the memory 110, are successively referred to in step S103, the rate of change in the time interval $\Delta t$ with respect to the relative position 304 can also be used as the condition for ending the movement of the relative position 304. More particularly, the movement of the relative position 304 is ended at the time when a change point of the rate of change illustrated in the graph of FIG. 3C (change point from [(302)+(303)] to [303] in the case of FIG. 3C) is discriminated. In the case of this form, the collimated propagation region 303 can be surely distinguished.

It is desirable that the range of movement of the relative position 304 measured in step S103 includes the range extending from the collecting process region 302 to the collimated propagation region 303, and the range extending again from the collimated propagation region 303 to the collecting process region 302 (region indicated by the dotted lines) in FIG. 3A. However, when the following condition that: the object used in step S103 is the object 109 which is actually used, and that a detecting region is defined in the range of movement of the relative position 304; is satisfied, the range of movement of the relative position 304 may include at least the range extending from the collecting process region 302 to the collimated propagation region 303 in FIG. 3A. In this case, the range of movement of the relative position 304 can be set to the range extending from the collecting process region 302 to the collimated propagation region 303. As is apparent from the measurement result of FIG. 3C, this is because the boundary from the collecting process region 302 to the collimated propagation region 303 (point from [(302)+(303)] to [(303)]) can be defined, and because it is assured that the time interval $\Delta t$ is not changed in the collimated propagation region 303 in which the time interval $\Delta t$ is measured. Further, when a detecting region is set by using a standard object, this condition can be applied as long as it is assured that the effective propagation length of a terahertz wave pulse in the standard object is longer than the effective propagation length of the terahertz wave pulse in the object 109 which is to be actually measured. More particularly, this condition can be applied as long as it is secured that the effective propagation length of a terahertz wave pulse in the standard object is longer than the effective propagation length of the terahertz wave pulse between the first reflecting surface 109a and the second reflecting surface 109b of the object 109, which are to be observed. This is because, when a detecting region is set by using a standard object, the effective propagation length of a terahertz wave pulse in the object 109 is short, and hence the first reflecting surface 109a and the second reflecting surface 109b are surely included in this detecting region.

The region designation unit 107 of the apparatus determines a detecting region by referring to the information on detecting regions (step S104). Here, the information on detecting regions is the information on the relative position 304 and the time interval $\Delta t$, which is stored in the memory 110. By referring to this information, the region designation unit 107 obtains a region (region [(303)] in FIG. 3C) where the time interval $\Delta t$ is not changed with respect to a change of the relative position 304, and sets a detecting region in this region.

Further, when, as shown in FIG. 1B, the database 111, in which the information on detecting regions measured beforehand is stored, is used instead of the region designation unit 107 and the memory 110, the above-described process is changed as follows. Step S101 and step S102 are omitted, and the information corresponding to these steps is measured beforehand and stored in the database 5111. In step S104 which is a process of determining a detecting region, the database 111 provides the information on the detecting region according to the form of the object 109 to be measured.

Figure 5A:
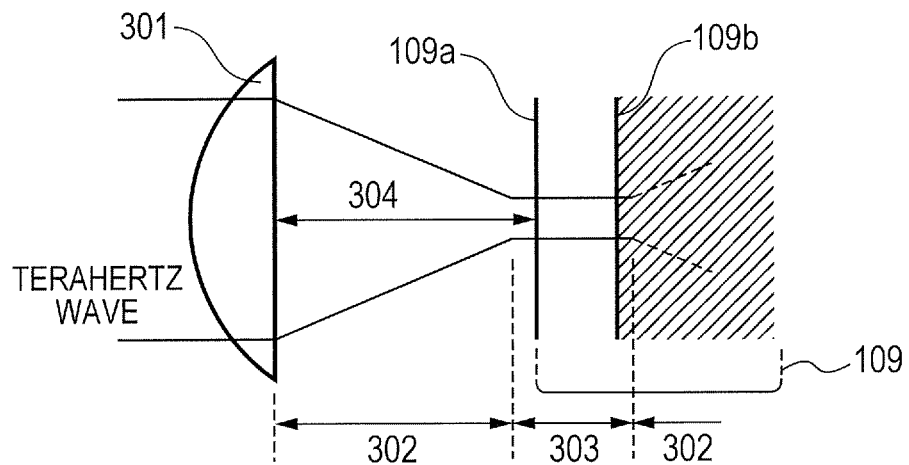
FIG. 5A and FIG. 5B are views describing results of adjustment of an object in the detecting region in exemplary embodiments 1 and 2.

After a detecting region is determined, then the apparatus adjusts the relative position 304 between the object 109 and the convergence unit 105 to the detecting region by using the adjustment unit 108 (step S105). More particularly, the relative position 304 is adjusted so that at least the first reflecting surface 109a and the second reflecting surface 109b, which are to be observed, are arranged in the collimated propagation region 303 as illustrated in FIG. 5A.

With the time waveform acquisition method of the exemplary embodiment, the detecting region, in which the measurement is performed, can be uniquely obtained from the information on the relative position between the object 109 and the convergence unit 105, and the information on the time interval between the pulses from the plurality of reflecting portions of the object 109. Further, at the time of acquiring a time waveform, the relative position is adjusted so that the portion of the object 109, which portion is to be observed, is included in the detecting region. For this reason, the positional relationship between the object 109 and the convergence unit 105 is stabilized, and hence the reliability of measurement accuracy is improved.

In the apparatus or method described above, a detecting region is determined by using the information on the time interval between terahertz wave pulses measured at the time when the object 109 is relatively moved in the range from the collimated propagation region 303 to the collecting process region 304 in the propagation shape of a terahertz wave pulse. When the object 109 is moved relatively in this range, it is possible to confirm the position at which the time interval between the terahertz wave pulses from the object 109 is changed. As a result, the detecting region can be specified, and thereby the interfaces of the object, which are to be observed, can be stably adjusted to the collimated propagation region of the terahertz wave.

A detecting region is determined by referring to the database 111 which is provided beforehand in the apparatus according to the form of the object 109. Alternatively, a detecting region is determined by measuring information on the relative position between the object 109 and the convergence unit 105, and information on the time interval between pulses from a plurality of reflecting portions of the object 109 at an arbitrary time after the object 109 is arranged. For this reason, the method can easily perform the measurement of the object 109 having various forms and properties, and thereby the flexibility of the method is improved.

In the apparatus or method described above, the detecting region is a region where the first reflecting surface 109a and the second reflecting surface 109b of the object 109 are included in the collimated propagation region 303. Since respective reflecting portions are in the collimated propagation region 303, the interval between the interfaces of the object is accurately reflected in the time interval between measured terahertz wave pulses. As a result, the reliability of each measurement is improved. Further, not only the information on the structure of the object 109 but also the physical properties of the object 109 can be acquired by utilizing the permeating characteristic and analyzing properties of a terahertz wave pulse.

EXAMPLE 1

In an example based on exemplary embodiment 1, an apparatus having the configuration of the apparatus of FIG. 1A is used. A photoconductive element is used as each of the generation unit 101 and the detection unit 102. Low-temperature-grown indium gallium arsenide (LT-GaInAs) is used as a semiconductor film of the generation unit 101. Low-temperature-grown gallium arsenide (LT-GaAs) is used as a semiconductor film of the detection unit 102. A dipole antenna having an antenna length of 20 μm and an antenna width of 10 μm is patterned on each of the semiconductor films. A gap portion having a width of 6 μm is formed at the center of the patterned dipole antenna. In order to improve the efficiency of taking in terahertz wave pulses, a super-hemispherical lens (having an offset of 1 mm) formed of high resistance silicon is brought into close contact with the semiconductor film at a position facing the patterned dipole antenna.

A femtosecond fiber laser having a center wavelength of 1.56 μm, a pulse width of 30 femtoseconds, and a repetition frequency of 50 MHz is used as the light source 103. The probe light $L_2$ is converted into femtosecond laser light having a center wavelength of 0.78 lam, and a pulse width of 70 femtoseconds by arranging a wavelength conversion element (PPLN) between the beam splitter BS and the delay optical unit (104). The pump light $L_1$ of 20 mW is made incident on the generation unit 101. The probe light $L_2$ of 1 mW is made incident on the detection unit 102. Each of the pump light $L_1$ and the probe light $L_2$ is shaped by each of the lenses $LE_1$ and $LE_2$ to have a beam diameter slightly less than 10 μm, and is made incident on the gap portion of the antenna pattern of each of the photoconductive elements. The delay optical unit 104 is configured by a linear movement stage and a retro-reflector. The position information on the linear movement stage is inputted into the waveform acquisition unit 106. The repetition positioning accuracy of the linear movement stage is 10 nm. The waveform acquisition unit 106 is configured by a current amplifier and an A/D board. The A/D board is connected to an arithmetic processing apparatus. The time waveform of a terahertz wave pulse is formed by successively plotting the outputs of the current amplifier, which correspond to the position information of the delay optical unit (104).

The convergence unit 105 is configured by four parabolic mirrors $M_4$ to $M_7$. The parabolic mirror $M_4$ shapes a terahertz wave pulse generated by the generation unit 101 into a parallel light beam. The parabolic mirror $M_5$ converges the terahertz wave pulse to the object 109, and the parabolic mirror $M_6$ shapes the reflected terahertz wave pulse into a parallel light beam. The focal length of the parabolic mirror is about 101 mm, and the calculated depth of focus of the terahertz wave pulse is several millimeters. The adjustment unit 108 is a stage which adjusts the distance between the object 109 and the convergence unit 105. The positioning resolution of the adjustment unit 108 is 100 μm. The signal output from the stage is inputted, as the change amount of the relative position 304, into the region designation unit 107. The region designation unit 107 is configured by an interface unit for performing communication with a driver used for driving the adjustment unit 108, and a processing unit for calculating a detecting region, and is mounted to the arithmetic processing apparatus. The interface unit mounted to the arithmetic processing unit also has a role of performing communication with the driver which controls the stage of the delay optical unit 104. A hard disk in the arithmetic processing apparatus is used as the memory 110.

Figure 16:
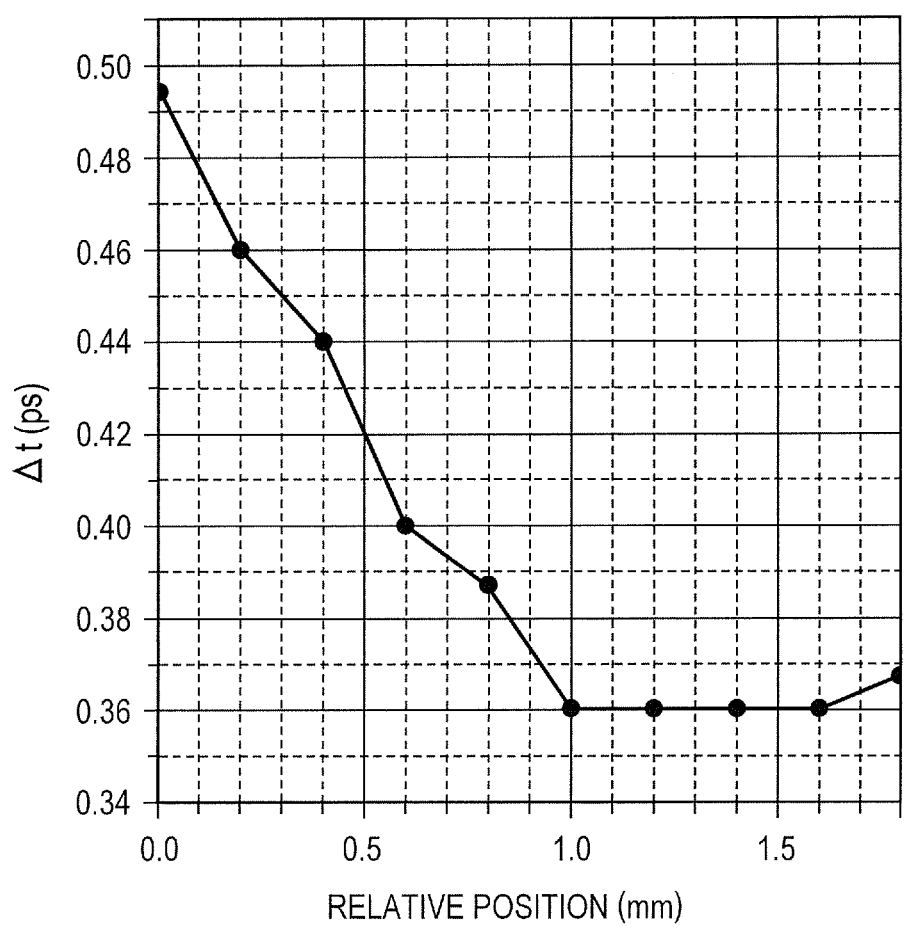
FIG. 16 is a view describing a result of processing of a region designation unit of example 1.

FIG. 16 is a relationship diagram between the relative position 304 set in the region designation unit 107 and the time interval Δt between terahertz wave pulses at the time when a porous film is used as the object 109. The object 109 has a thickness of about 30 μm, and is placed on a gold substrate. In this example, the time interval Δt is monitored in a state where the first reflecting surface 109a of the object 109 is set as the surface of the porous film, and the second reflecting surface 109b is set as the interface between the porous film and the gold substrate. In this example, the relative position 304 corresponding to the initial position of the adjustment unit 108 is set to 0 mm. It was confirmed from FIG. 16 that, as the relative position 304 is increased, the time interval Δt between terahertz wave pulses is reduced, and that when the relative position 304 exceeds 1 mm, the time interval Δt is substantially fixed. Further, it was confirmed that, when the relative position 304 exceeds 1.6 mm, the time interval Δt tends to be again increased. In this example, a range of 1.0 mm to 1.6 mm of the relative position 304 is defined as the collimated propagation region 303 by the region designation unit 107. Further, the detecting region is set to a range of 1.1 mm to 1.5 mm of the relative position 304 in consideration of the positioning resolution of the adjustment unit 108. At the time of measuring the object 109, the apparatus in this example adjusts the relative position 304 by the adjustment unit 108 so that the object 109 is included in this detecting region.

Note that, in this example, the relative position 304 is adjusted by moving the object 109, but as described in exemplary embodiment 1, the converging position of the electromagnetic waves, such as a terahertz wave pulse, may be moved by using the convergence unit 105, the generation unit 101, and the detection unit 102 in a state where the object 109 is fixed. This form of the apparatus is preferred because, when it is difficult to move the side of the object 109 in correspondence with the adjustment unit 108 as in the case where the object 109 is a part of a human body or a living thing, the measurement can be performed in a state where the object 109 is fixed.

(Exemplary Embodiment 2)

Exemplary embodiment 2 which can carry out the spirit of the present invention will be described with reference to the accompanying drawings. Specifically, the exemplary embodiment is related to an installation form of the object 109. Note that portions in common with the portions described above are omitted.

Figure 4:
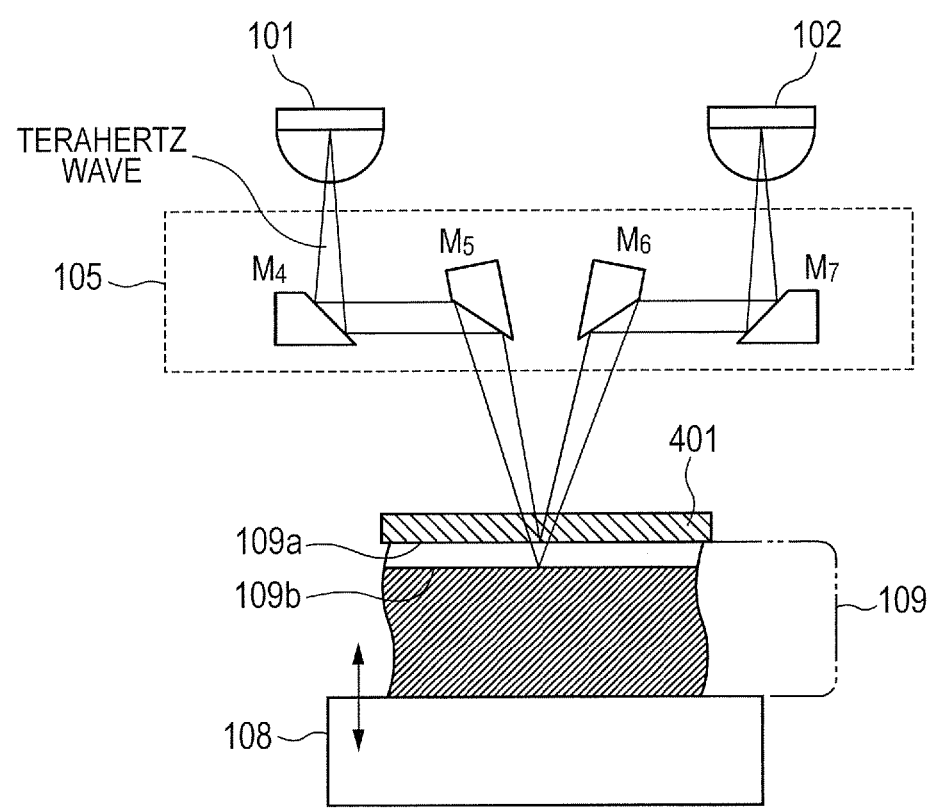
FIG. 4 is a view describing an installation form of an object of exemplary embodiment 2.

FIG. 4 is a view describing an installation form of the object 109 in the exemplary embodiment. The exemplary embodiment is different from the above-described exemplary embodiment and the above-described example in that a measurement surface formation member 401 is arranged in close contact with the object 109. More particularly, the measurement surface formation member 401 is arranged in close contact with the surface of the object 109, on which surface a terahertz wave pulse is made incident. When the measurement surface formation member 401 and the object 109 are brought into close contact with each other, the boundary surface between the measurement surface formation member 401 and the object 109 is reformed into the shape of the measurement surface formation member 401. In the case where the object 109 is made of a soft material, such as a living body or a foodstuff, the flatness of the reflecting portion is increased by the reformation of the boundary surface. A plurality of reflected pulses, each of which reaches the detection unit 102 at a slightly different time from the region irradiated with a terahertz wave pulse, appear depending on the flatness of the reflection portion. In this case, these pulses arrive at the detection unit 102 in a state where these pulses interfere with each other. As a result, for example, a phenomenon in which the pulse width of the reflected pulse of FIG. 3B is increased, and a phenomenon in which the intensity of the pulse is reduced are caused. In particular, the typical beam diameter of a terahertz wave pulse is as large as sub-millimeters, and hence the influence of the shape of the reflecting portion is large. The measurement surface formation member 401 reshapes the shape of the reflecting portion of the object 109 into a shape (flat surface in FIG. 4) suitable for the measurement, to thereby reduce the influence of the shape of the object 109.

The measurement surface formation member 401 is arranged in the propagation path of a terahertz wave pulse, and hence a material having excellent transmissivity of the terahertz wave pulse is preferred as the material of the measurement surface formation member 401. For example, a resin, such as polyethylene, polytetrafluoroethylene as carbon fluoride resin, and cycloolefin polymer are applicable. A porosified form of the resin material is also applicable. Further, a substrate material, such as high resistance silicon and CVD (Chemical Vapor Deposition) diamond, is applicable. It is desirable that the flatness of the measurement surface formation member 401 is a degree that a terahertz wave pulse cannot recognize the structure of the measurement surface formation member 401. Specifically, it is desirable that, with respect to the effective wavelength λ of a terahertz wave pulse to be used (typically the center wavelength of the spectrum of the terahertz wave pulse), the flatness of the measurement surface formation member 401 is in the range of 1/100 λ to 1/20λ. For example, it is desirable that, when λ is 100 μm, the flatness of the measurement surface formation member 401 is in the range of about 1 to 5 μm. Under this condition, the influence of scattering of the terahertz wave pulse by the measurement surface formation member 401 can be suppressed. The flatness of the measurement surface formation member 401 depends also on the accuracy required for optically measuring the first reflecting surface 109a and the second reflecting surface 109b. For example, when these reflecting portions are to be directly measured with an accuracy of 10 μm, it is desirable that the flatness of the measurement surface formation member 401 is smaller than this value of accuracy. When a measurement error is defined as a measurement specification, it is desirable that the flatness is smaller than this measurement error.

Figure 5B:
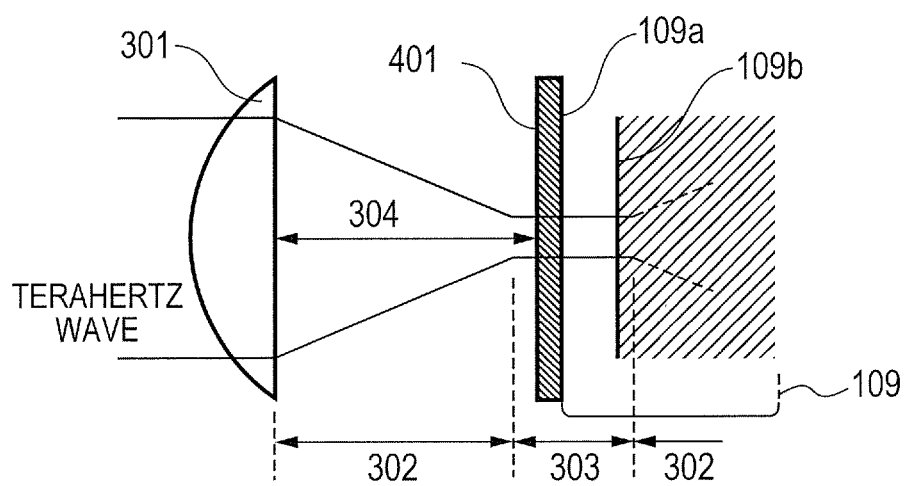

FIG. 5B is a view describing the result of adjustment of the object 109 to the detecting region at the time of applying the measurement surface formation member 401. When the measurement surface formation member 401 is placed in the propagation path of a terahertz wave pulse, it is desirable to also accurately measure the physical properties of the measurement surface formation member 401 in the terahertz wave region in order to accurately measure the physical properties of the region sandwiched between the first reflecting surface 109a and the second reflecting surface 109b which are to be observed. More particularly, the physical property information of the measurement surface formation member 401 is removed from the measurement result of the first reflecting surface 109a and the second reflecting surface 109b. The processing is performed in such a manner that, based on the physical property information of the measurement surface formation member 401, the measurement condition of a terahertz wave pulse is virtually reconstructed from the state of FIG. 5B to the state of FIG. 5A, and then analysis is performed. For this reason, when the physical properties of the region sandwiched between the first reflecting surface 109a and the second reflecting surface 109b is handled by using the measurement surface formation member 401, the detecting region is set in a region which includes the first reflecting surface 109a and the second reflecting surface 109b of the object 109 to be observed, and the measurement surface formation member 401. In view of this, the thickness of the measurement surface formation member 401 is set in a range not larger than the difference between the detecting region and the reflecting portion to be observed. However, a part of the measurement surface formation member 401 may be located outside the detecting region. For example, in such an application in which a change in the optical distance between the first reflecting surface 109a and the second reflecting surface 109b is monitored, it is only necessary that a change in the first pulse 305 and the second pulse 306 can be measured. Therefore, a part of measurement surface formation member 401 may be located outside the detecting region.

Note that the measurement surface formation member 401 of FIG. 4 has a shape of a planar substrate, but the shape of the measurement surface formation member 401 is not limited to this. For example, the measurement surface formation member 401 may be partially provided with a protruding and recessed shape, so as to additionally have a function of further reshaping a terahertz wave pulse. Further, when the object 109 has large fluidity, the measurement surface formation member 401 may be provided with a protruding and recessed shape, so as to additionally have a function of collecting the object 109 in a predetermined place. Also in such a case, the same measurement principle can be applied.

In the time waveform acquisition apparatus and method of the exemplary embodiment, the measurement surface formation member 401 is brought into close contact with the object 109, and thereby the shape of the surface, through which an electromagnetic wave pulse is made incident on the object 109, is reformed into a shape corresponding to the external shape of the measurement surface formation member 401. For this reason, when this incident surface is used as one reflecting portion, the shape of the surface, through which a terahertz wave pulse is made incident on the object 109, becomes close to a reflecting surface suitable for the apparatus. As a result, the measurement accuracy of the time interval of terahertz wave pulses from the object 109 for a relative position is improved, and thereby the detecting region can be easily determined.

(Exemplary Embodiment 3)

Exemplary embodiment 3 which can carry out the spirit of the present invention will be described with reference to the accompanying drawings. Specifically, the exemplary embodiment relates to a modification of the portion of adjusting the relative position 304 described above. Note that portions in common with the portions described above are omitted.

Figure 7A:
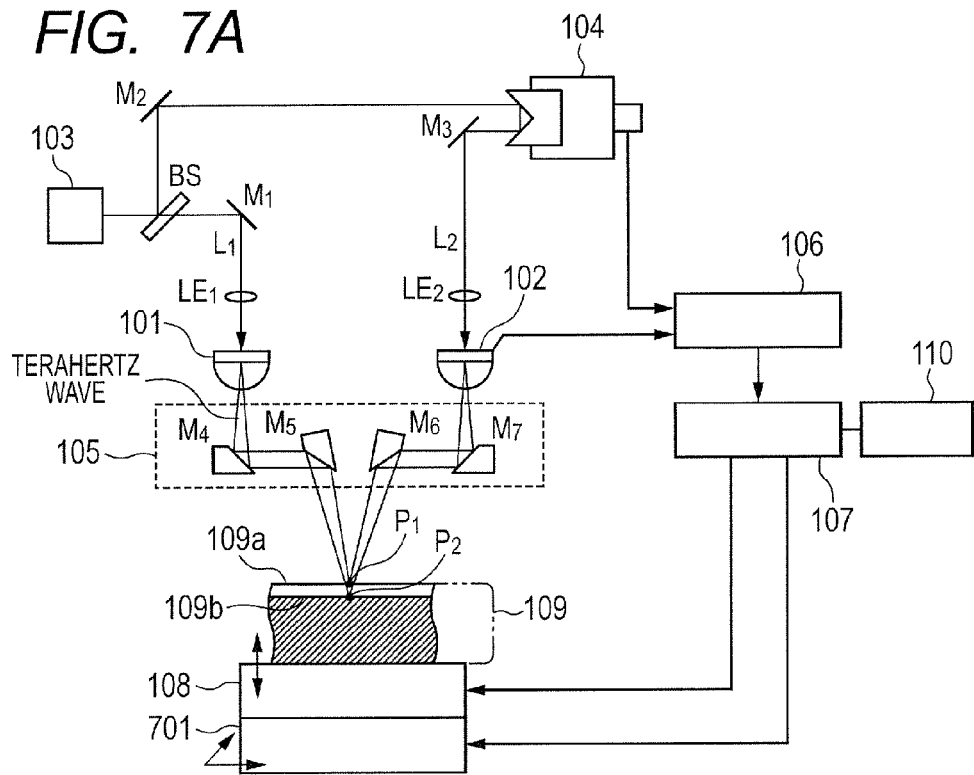
FIG. 7A and FIG. 7B are views illustrating a schematic configuration of an apparatus of exemplary embodiment 3.

FIG. 7A is a view illustrating a schematic configuration of an apparatus of the exemplary embodiment. The exemplary embodiment is different from the above described apparatuses in that a cross-sectional position adjustment unit 701 is added to the portion of adjusting the relative position 304 between the convergence unit 105 and the object 109. The cross-sectional position adjustment unit 701 is a portion which adjusts the relative position between the object 109 and the convergence unit 105 in the cross-sectional direction crossing the propagation direction of a terahertz wave pulse converged by the convergence unit 105. In the form of the apparatus of FIG. 7A, the cross-sectional position adjustment unit 701 is configured by a stage which moves the object 109 in the cross-sectional direction with respect to the propagation direction of a terahertz wave pulse. However, it is only necessary that the position of the object 109 is moved relatively to the terahertz wave pulse, and hence a form, in which the generation unit 101, the detection unit 102, the convergence unit 105, and the optical system provided in association with these units are moved in the cross-sectional direction, may also be adopted. Here, the cross-sectional direction is expressed as the direction crossing the propagation direction of a terahertz wave pulse, but can also be rephrased as follows. The cross-sectional direction is along the surface normal to the driving direction of the adjustment unit 108.

Figure 8A:
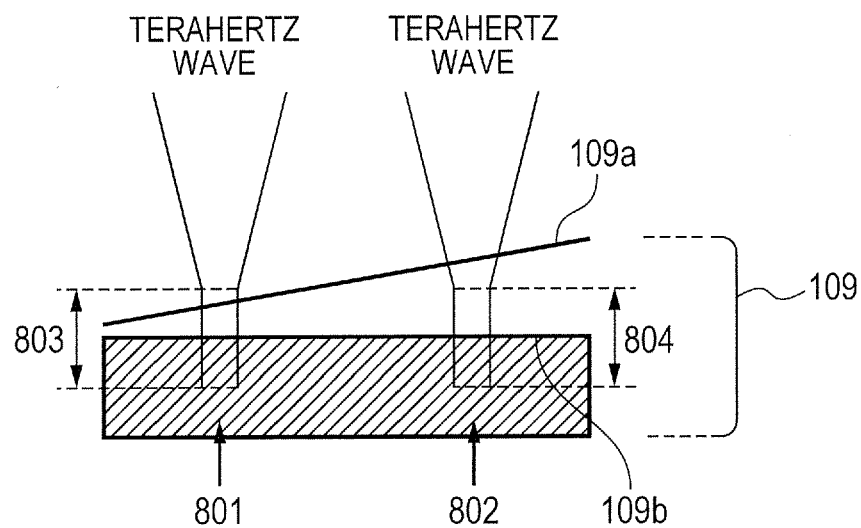
FIG. 8A and FIG. 8B are views describing an operation of the apparatus of exemplary embodiment 3.
Figure 8B:
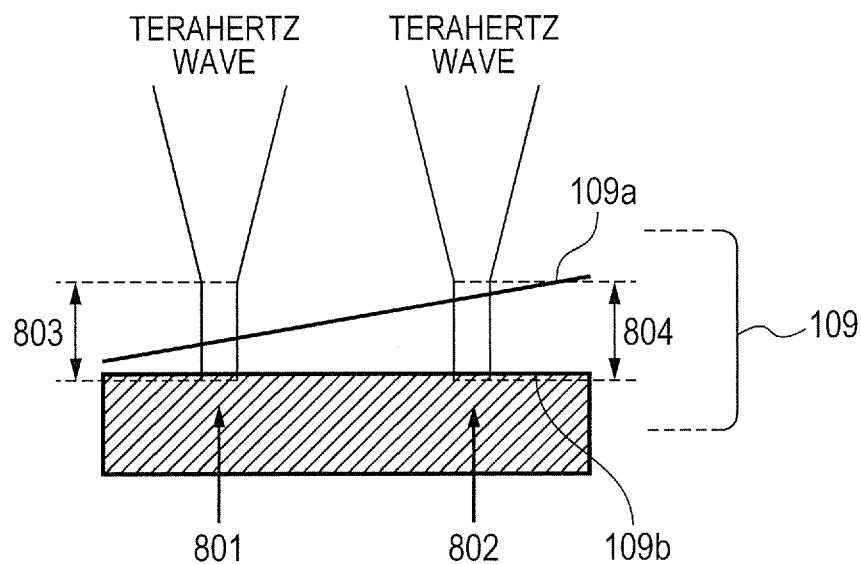

FIG. 8A and FIG. 8B describe operation of the apparatus. In the case where measurement is performed at a plurality of portions of the object 109, it is desirable that the first reflecting surface 109a and the second reflecting surface 109b, which are to be measured at the respective measurement places, are included in a detecting region set in the inside of the collimated propagation region 303. As in the case of FIG. 8A, a part of the reflecting portion is deviated from the collimated propagation region 303 depending on the form of the first reflecting surface 109a and the second reflecting surface 109b of the object 109. For example, in FIG. 8A, the first reflecting surface 109a of the object 109 is included in a first collimated propagation region 803 at a first position 801, but is deviated from a second collimated propagation region 804 at a second position 802. In the exemplary embodiment, the position of the object 109 is three-dimensionally adjusted by using the adjustment unit 108 and the cross-sectional position adjustment unit 701. As a result, as in FIG. 8B, the first reflecting surface 109a and the second reflecting surface 109b of the object 109 can be adjusted so as to be included in the first collimated propagation region 803 and the second collimated propagation region 804. A detecting region is set by referring to this information so that the first reflecting surface 109a and the second reflecting surface 109b are respectively included in the collimated propagation region. Note that two or more measurement places of the terahertz wave pulse may be provided.

Figure 9:
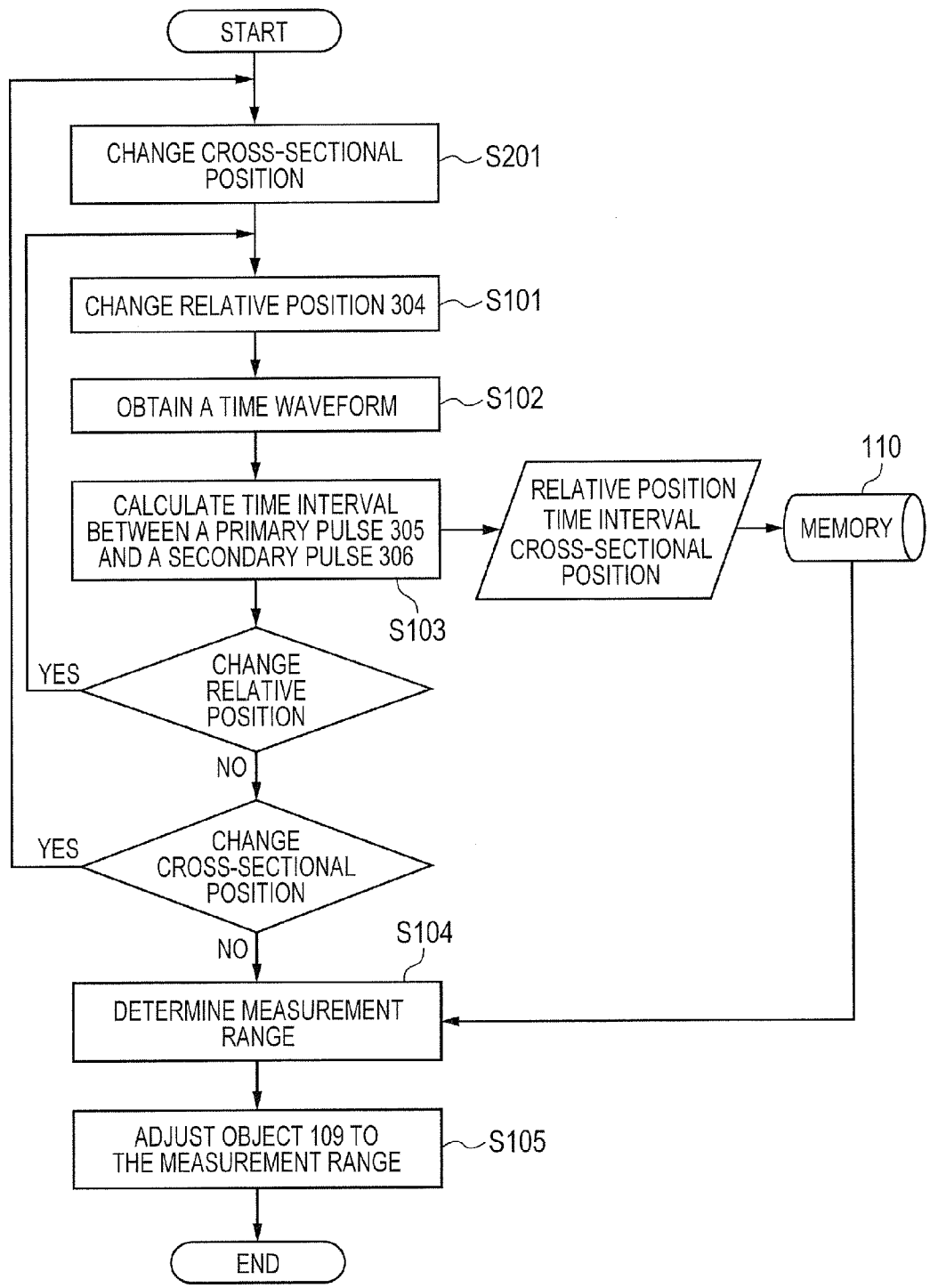
FIG. 9 is a flow chart describing a measurement method of the apparatus of exemplary embodiment 3.

FIG. 9 is a flow chart describing a method used in the apparatus of the exemplary embodiment. When the operation of the apparatus is started, the apparatus moves the cross-sectional position of the object 109 by using the cross-sectional position adjustment unit 701 (step S201). Further, the apparatus may have such a form that, only at the time of beginning of operation, the object 109 is moved to a predetermined position determined by a measurer, and that, in the subsequent process, the object 109 is moved based on the predetermined position.

When the movement of the object 109 in the cross-sectional direction is ended, the apparatus obtains a relationship between the relative position 304 and the time interval Δt by repeating the process from step S101 to step S103 described above. In the process of step S103, in addition to the relative position 304 and the time interval Δt, the apparatus stores, in the memory 110, the information on the cross-sectional direction position. After the movement of the relative position 304 is ended, the apparatus confirms the condition to end the movement of the cross-sectional direction position. When the condition to end the movement of the cross-sectional direction position is not satisfied, the process returns to step S201. This ending condition can be defined, for example, as follows. Positions, to which the cross-sectional position adjustment unit 701 moves the object 109, are defined beforehand, and the ending condition is set to the time when all of the movement of the object 109 to the respective positions is ended. The positions, to which the cross-sectional position adjustment unit 701 moves the object 109, are determined by the measurer by referring to a region scheduled to be measured. Further, the apparatus may have such a form that, when the object 109 additionally has a portion whose external appearance, and the like, is to be checked, or when the external appearance of the object 109 is known in advance, feature points, such as points of different thickness, are recognized by the apparatus, and that the positions, to which the object 109 is moved, are defined with respect to the feature points. Further, the positions, to which the object 109 is moved, may be defined by using a measurement position pattern prepared by the apparatus, irrespective of the region which is set to be measured by the measurer. The measurement-point pattern prepared by the apparatus includes a plurality of candidates, which are suitably selected by the measurer according to the form of the object 109.

Figure 7B:
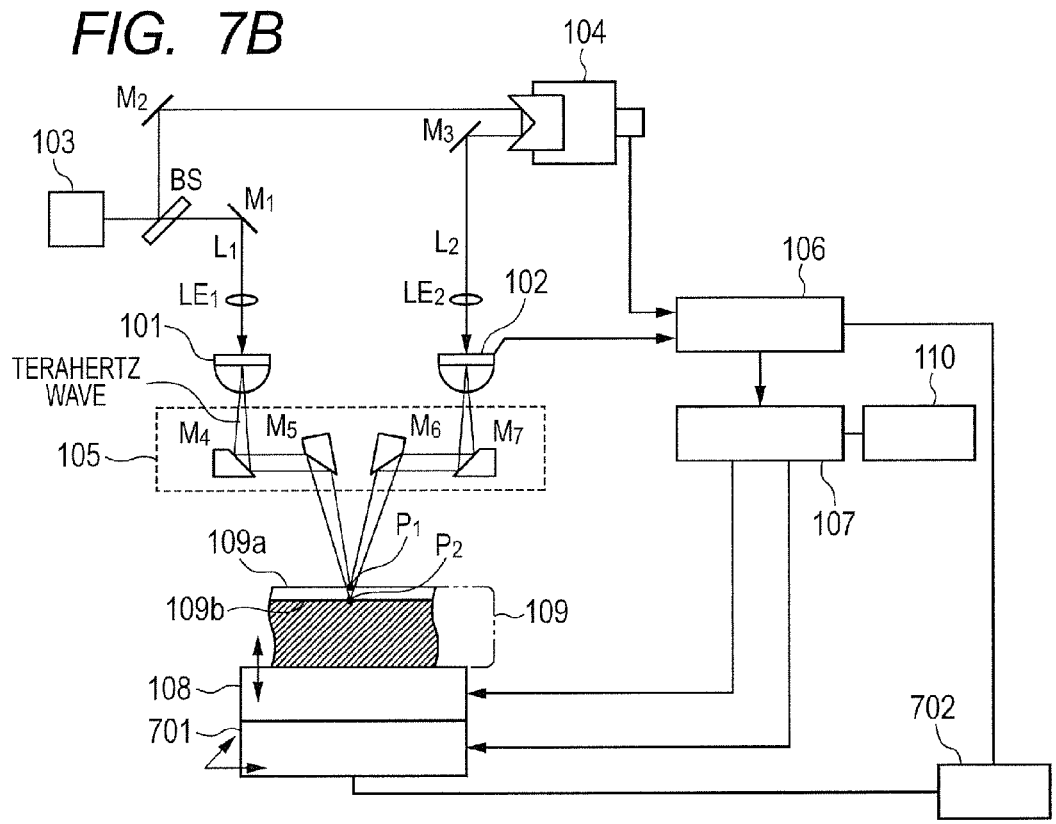

When the movement of the cross-sectional direction position is ended, the apparatus sets a detecting region in step S104, and moves the object 109 to the detecting region in step S105. A tomography apparatus, the schematic configuration of which is illustrated in FIG. 7B, can be configured by using the measuring apparatus configured as described above. The tomography apparatus includes an image constructing unit 702 which constructs a tomographic image of an object by processing in which the relative position adjusted by the cross-sectional position adjustment unit is made to correspond to the interval information obtained by using the detection result of the detection unit.

With the time waveform acquisition apparatus and method of the exemplary embodiment, the relative position between the object 109 and the convergence unit 105 can be moved by the cross-sectional position adjustment unit 108 in the cross-sectional direction crossing the propagation direction of an electromagnetic wave, such as a terahertz wave pulse. Further, at a plurality of positions of the object 109, the relative position is adjusted so that the portions of the object 109, which are to be observed, are included in the detecting region. For this reason, the measurement of the object 109 can be stably performed over a wider region, and hence the flexibility of the apparatus and method is improved.

(Exemplary Embodiment 4)

Exemplary embodiment 4 which can carry out the spirit of the present invention will be described with reference to the accompanying drawings. Specifically, the exemplary embodiment is a modification of the portion of adjusting the relative position 304 described above. Note that portions in common with the portions described above are omitted.

Figure 10:
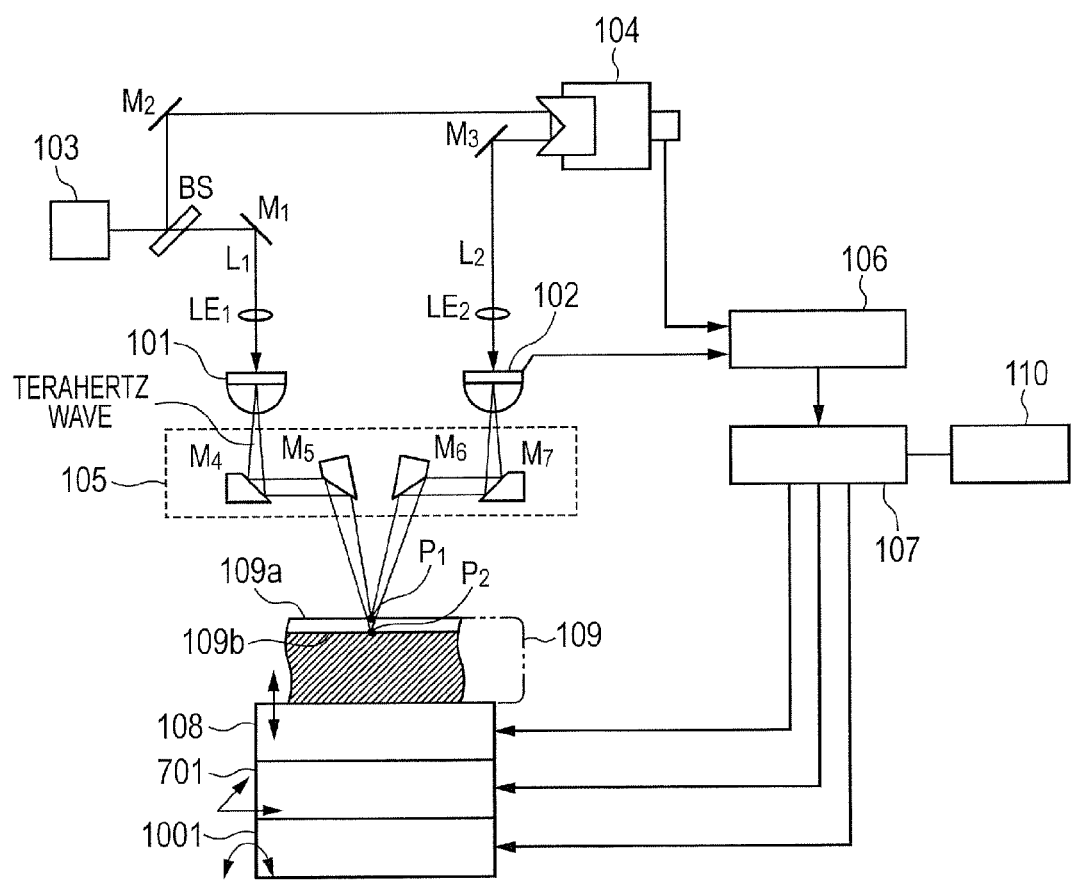
FIG. 10 is a view illustrating a schematic configuration of an apparatus of exemplary embodiment 4.

FIG. 10 is a view illustrating a schematic configuration of an apparatus of the exemplary embodiment. The exemplary embodiment is different from the above described apparatuses in that an incident angle adjustment unit 1001 is further added to the portion of adjusting the relative position 304 between the convergence unit 105 and the object 109 in the configuration of the apparatus in exemplary embodiment 3. The incident angle adjustment unit 1001 is a portion which adjusts the relative angle between the object 109 and the convergence unit 105 in association with the incident angle of a terahertz wave pulse converged by the convergence unit 105 to the object 109. In the form of FIG. 10, the incident angle adjustment unit 1001 is configured by a stage which adjusts the angle of the object 109 with respect to the incidence direction of the terahertz wave pulse. However, it is only necessary that the angle of the object 109 is moved relatively to the incident direction of the terahertz wave pulse, and hence a form, which moves the angle of the generation unit 101, the detection unit 102, the convergence unit 105, and the optical system provided in association with these, may also be applied.

Figure 11A:
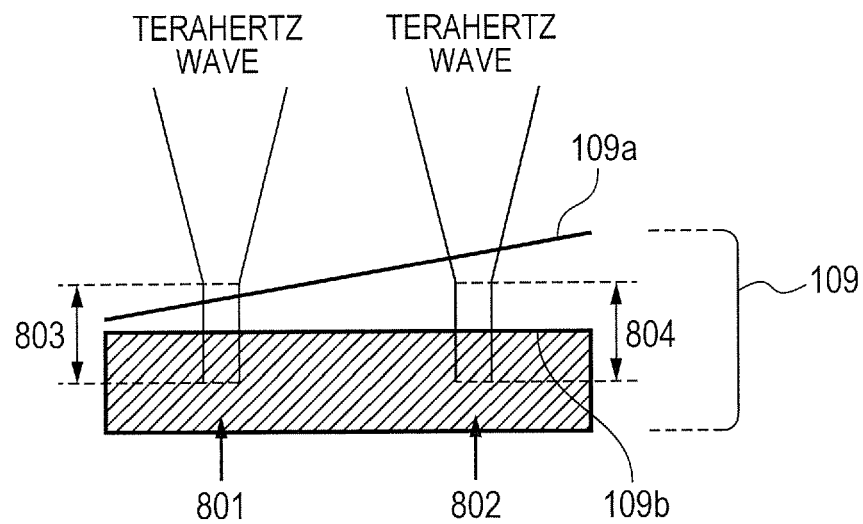
FIG. 11A and FIG. 11B are views describing an operation of the apparatus of exemplary embodiment 4.
Figure 11B:
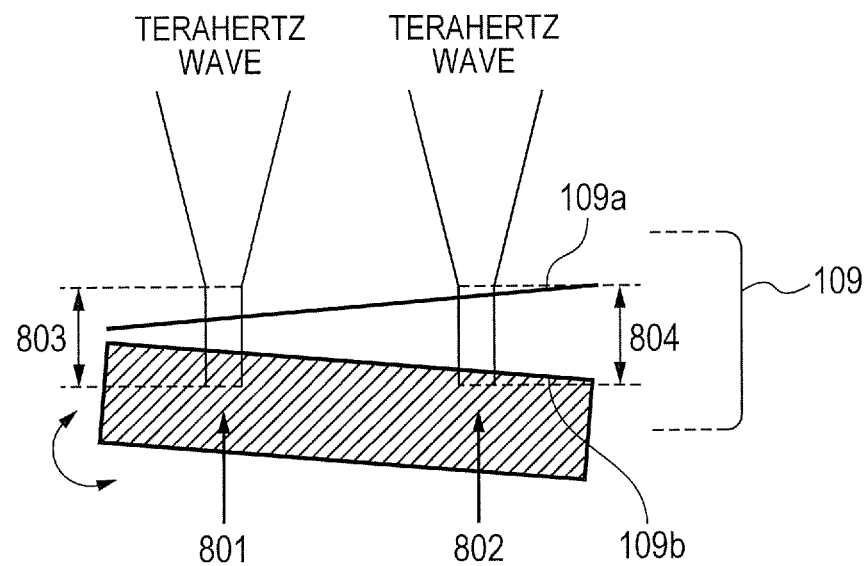

FIGS. 11A and 11B are views describing the operation of the apparatus. As also described in exemplary embodiment 3, it is desirable that, when the apparatus performs measurement at a plurality of places of the object 109, the first reflecting surface 109a and the second reflecting surface 109b, which are to be measured at the respective measurement places, are included in a detecting region set in the collimated propagation region 303. As in the case of FIG. 11A, a part of the reflecting portion may be deviated from the collimated propagation region 303 depending on the form of the first reflecting surface 109a and the second reflecting surface 109b of the object 109. For example, in FIG. 11A, the first reflecting surface 109a of the object 109 is included in the first collimated propagation region 803 at the first position 801 but is deviated from the second collimated propagation region 804 at the second position 802. In the exemplary embodiment, the position of the object 109 is three-dimensionally adjusted by using the incident angle adjustment unit 1001 in addition to the adjustment unit 108 and the cross-sectional position adjustment unit 701. In the exemplary embodiment, the adjustment means of angular orientation is added, and hence the flexibility in adjustment of the position of the object 109 is improved as compared with the form of exemplary embodiment 3. As a result of adjustment of the position of the object 109, as in FIG. 11B, the first reflecting surface 109a and the second reflecting surface 109b of the object 109 can be adjusted so as to be included in the first collimated propagation region 803 and the second collimated propagation region 804. By referring to this information, a detecting region is set so that the first reflecting surface 109a and the second reflecting surface 109b are respectively included in the collimated propagation region. Note that two or more measurement places of the terahertz wave pulse may be provided.

Figure 12:
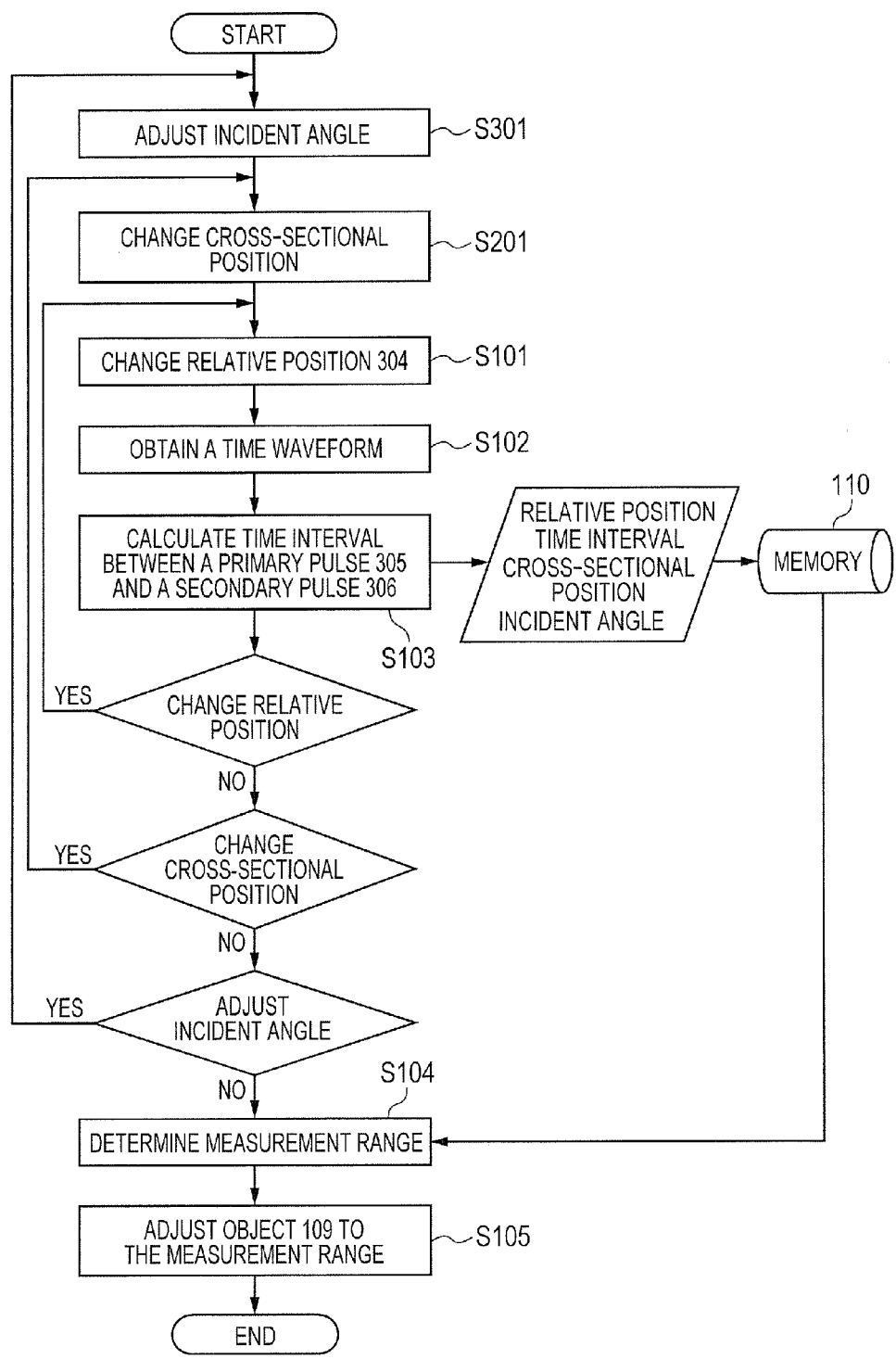
FIG. 12 is a flow chart describing a measurement method of the apparatus of exemplary embodiment 4.

FIG. 12 is a flow chart describing a method used in the apparatus of the exemplary embodiment. When the operation of the apparatus is started, the apparatus adjusts the incident angle of a terahertz wave pulse with respect to the object 109 by using the incident angle adjustment unit 1001 (step S301). The apparatus may have such a form that, only at the time of beginning of operation, the object 109 is adjusted at a predetermined incident angle determined by the measurer, and that, in the subsequent process, the object 109 is adjusted based on the predetermined incident angle. When the adjustment of the incident angle is ended, the apparatus obtains a relationship between the relative position 304 and the time interval Δt by repeating the process from step S101 to step S103 described above. In the process of step S103, the apparatus stores the information on the incident angle in the memory 110 in addition to the relative position 304 and the time interval Δt.

After the movement of the relative position 304 and the movement of the cross-sectional position are ended, the apparatus confirms the condition to end the adjustment of incident angle. When the condition to end the adjustment of incident angle is not satisfied, the process returns to step S301. This ending condition can be defined, for example, as follows. That is, in the case where a range in which the incident angle is changed is specified beforehand, the condition that the total range of changes, each made by a predetermined amount of incident angle in the specified range, covers the whole specified range is set as the ending condition. Further, in the case where, from the present incident angle, the incident angle is changed in the direction of increasing the incident angle and in the direction of reducing the incident angle, results of comparison of the sizes and boundaries of the respective collimated propagation region in the three directions may also be used as the ending condition. In the case where the sizes of the respective collimated propagation regions are compared with each other, the condition that the size of the collimated propagation region at the present incident angle is the largest or is not changed as compared with the size of the collimated propagation region at the time when the incident angle is changed in the directions of increasing and decreasing the incident angle is set as the ending condition. Further, in the case where the boundaries of the respective collimated propagation regions are compared with each other, the condition that the deviations of the relative positions respectively corresponding to the boundaries of the collimated propagation region at the present incident angle is the smallest as compared with the deviations of the relative positions respectively corresponding to the boundaries of the collimated propagation region at the time when the incident angle is changed in the directions of increasing and decreasing the incident angle is set as the ending condition. Each of the incident angles changed in the directions of increasing and decreasing the incident angle is used as the incident angle to be compared, but the ending condition can also be determined by using only one of the incident angles changed in the directions of increasing and decreasing the incident angle.

When the adjustment of the incident angle is ended, the apparatus sets a detecting region in step S104, and moves the object 109 to the detecting region in step S105.

With the time waveform acquisition apparatus and method of the exemplary embodiment, the incident angle of an electromagnetic wave made incident on the object 109 can be adjusted by the incident angle adjustment unit 1001. Further, in a plurality of positions of the object 109, in parallel with the adjustment of the relative position, the incident angle is adjusted so that the portions of the object 109, which are to be observed, are included in the detecting region. For this reason, the measurement of the object 109 can be stably performed over a wider region, and hence the flexibility of the apparatus and method is improved. Further, when the incident angle of the electromagnetic wave from the portion of object 109, which portion is to be observed, is adjusted so that the output of the detection unit 102 is increased, the detection sensitivity of a signal is improved. Thereby, the SN ratio of the signal is improved, and hence the reliability of measurement accuracy is improved.

(Exemplary Embodiment 5)

Exemplary embodiment 5 which can carry out the spirit of the present invention will be described with reference to the accompanying drawings. Specifically, the exemplary embodiment is a modification of the portion of adjusting the relative position 304 described above. More specifically, it is a modification of the apparatus described in exemplary embodiment 4. Note that portions in common with the portions described above are omitted.

Figure 13:
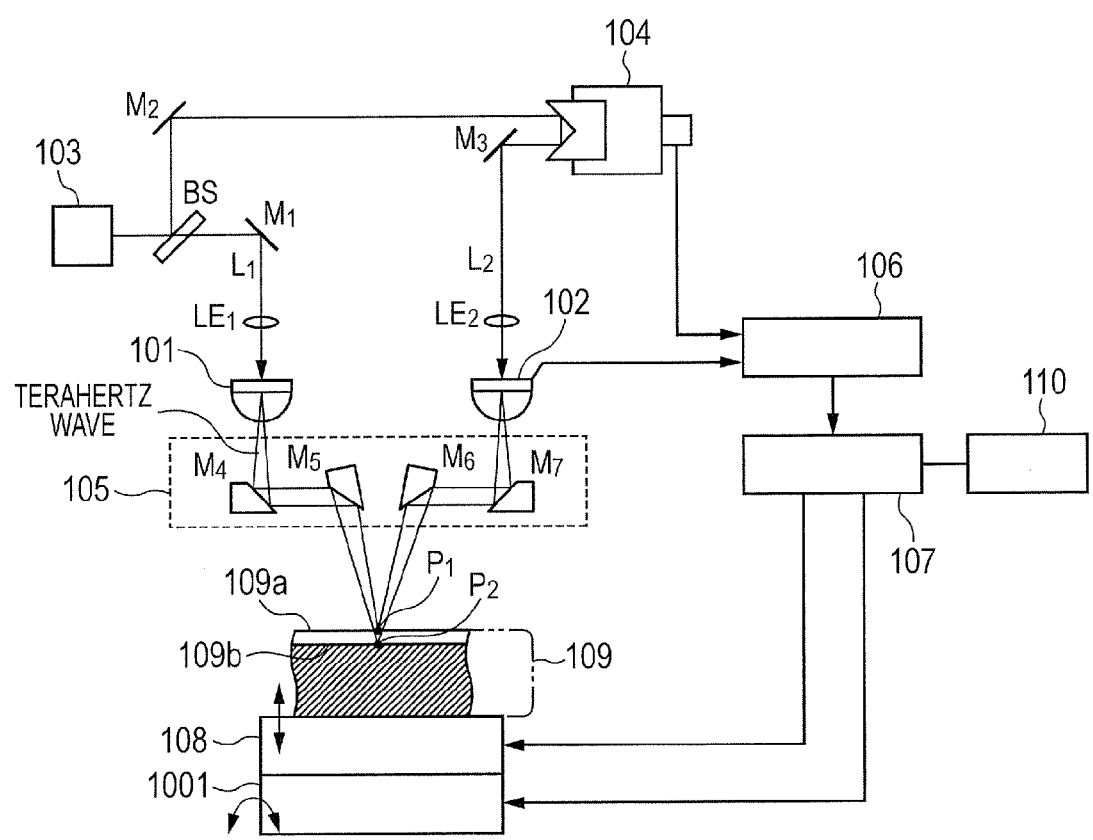
FIG. 13 is a view illustrating a schematic configuration of an apparatus of exemplary embodiment 5.

FIG. 13 is a view illustrating a schematic configuration of an apparatus of the exemplary embodiment. When the apparatus of the exemplary embodiment is compared with the exemplary embodiment illustrated in FIG. 10, the apparatus of the exemplary embodiment is different in that the portion for adjusting the relative position 304 is configured by the adjustment unit 108 and the incident angle adjustment unit 1001. The incident angle adjustment unit 1001 of the exemplary embodiment has the same function as the function of the incident angle adjustment unit 1001 described in exemplary embodiment 4.

Figure 14A:
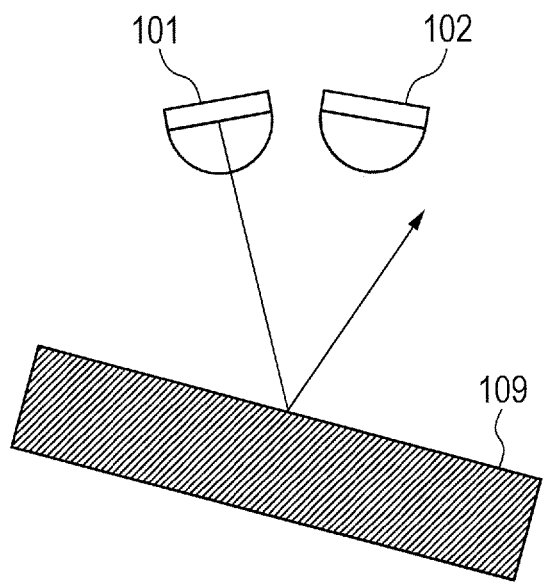
FIG. 14A and FIG. 14B are views describing an operation of the apparatus of exemplary embodiment 5.
Figure 14B:
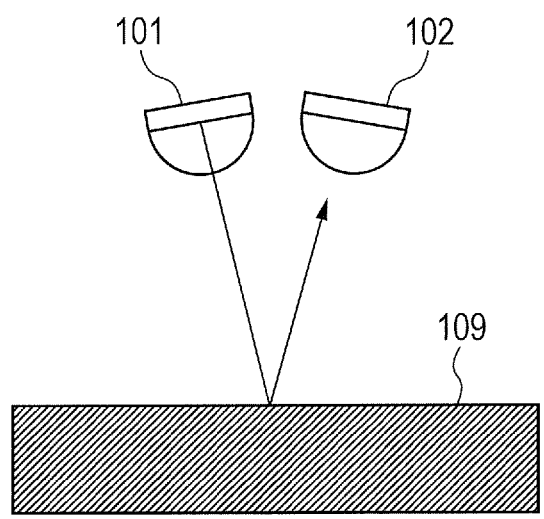

The apparatus is operated as illustrated in FIG. 14A and FIG. 14B. When the relative position 304 is adjusted, there is a case where, depending on the incident angle of a terahertz wave pulse made incident on the object 109, the path of the reflected terahertz wave pulse is deviated from the detection unit 102 as illustrated in FIG. 14A, and thereby the signal intensity of the output of the detection unit 102 is reduced. Therefore, in the exemplary embodiment, the incident angle adjustment unit 1001 adjusts, as illustrated in FIG. 14B, the incident angle of the terahertz wave pulse made incident on the object 109, so as to make the reflected terahertz wave pulse incident on the detection unit 102. As a result, the ratio of the signal output from the detection unit 102 to noise is increased, and hence the measurement accuracy can be improved.

Figure 15:
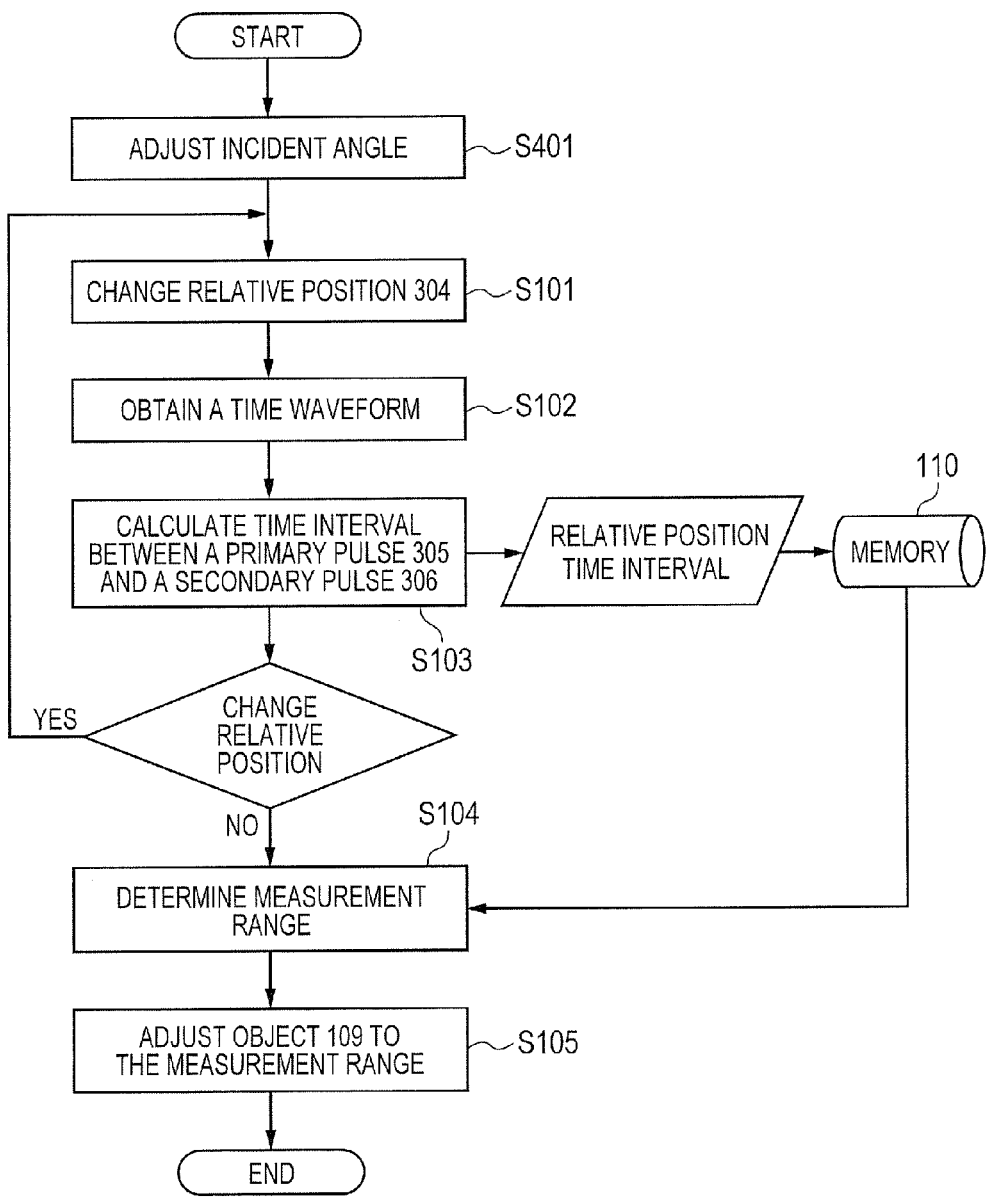
FIG. 15 is a flow chart describing a measurement method of the apparatus of exemplary embodiment 5.

FIG. 15 is a flow chart describing a method used in the apparatus of the exemplary embodiment. When the operation of the apparatus is started, the apparatus adjusts the incident angle of a terahertz wave pulse with respect to the object 109 by using the incident angle adjustment unit 1001 so that the output of the detection unit 102 becomes a maximum (step S401). When the adjustment of the incident angle is ended, the apparatus sets, as described above, a detecting region by the process of step S101 to step S105 and adjusts the object 109 to the detecting region.

With the time waveform acquisition apparatus and method of the exemplary embodiment, the incident angle of an electromagnetic wave from the object 109 to be observed is adjusted so that the output of the detection unit 102 is increased. As a result, the detection sensitivity of the signal output from the detection unit 102 is improved. Thereby, the SN ratio of a signal is improved, and hence the reliability of measurement accuracy is improved.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-135260, filed Jun. 14, 2012, which is hereby incorporated by reference herein in its entirety.

What is claimed is:

1. A measuring apparatus for measuring an object, the object having a first reflecting surface and a second reflecting surface along a propagation path of an electromagnetic wave, the measuring apparatus comprising:
   a convergence unit for converging the electromagnetic wave to the object that is to be measured;
   a detection unit for detecting electromagnetic waves from the object; and
   an adjustment unit for adjusting a relative position between the object and the convergence position set by said convergence unit, and arranging the first reflecting surface and the second reflecting surface in a detecting region,
   wherein the detecting region is determined by using a plurality of pieces of information about the relative position, and information about a time interval between a first electromagnetic wave from the first reflecting surface and a second electromagnetic wave from the second reflecting surface in a time waveform acquired by using a detection result provided by said detection unit for the relative position corresponding to each of the plurality of pieces of information.

2. The measurement apparatus according to claim 1, further comprising one of
   a memory for beforehand storing information about the detecting region, and
   a region designation unit for designating the detecting region.

3. The measurement apparatus according to claim 1, wherein
   the plurality of pieces of information about the relative position is in a range between a relative position corresponding to a place where the value of the information about the time interval information is fixed, and a relative position corresponding to a place where the value of the information about the time interval information is again increased.

4. The measurement apparatus according to claim 1, further comprising
   a cross-sectional position adjustment unit which, in order to adjust the relative position between the object and the convergence position set by said convergence unit, adjusts the relative position in the cross-sectional direction crossing the propagation direction of the electromagnetic wave converged by said convergence unit.

5. The measurement apparatus according to claim 1, further comprising
   an incident angle adjustment unit which, in order to adjust the incident angle of the electromagnetic wave converged by said convergence unit to the object, adjusts the relative angle between the object and said convergence unit.

6. The measurement apparatus according to claim 1, further comprising a measurement surface formation member arranged in close contact with the surface of the object, the electromagnetic wave being made incident on the surface of the object.

7. The measurement apparatus according to claim 1, wherein the electromagnetic wave is a terahertz wave pulse.

8. A tomography apparatus comprising:
   the measurement apparatus according to claim 4; and an image constructing unit which constructs a tomographic image of the object by making the relative position set by the cross-sectional position adjustment unit correspond to the time interval information obtained by using the detection result provided by said detection unit.

9. A measurement method of an object, the object having a first reflecting surface and a second reflecting surface along a propagation path of an electromagnetic wave, the measurement method comprising
- a process of detecting electromagnetic waves from the object that is to be measured; and
- a process of adjusting a relative position between the object and a convergence position at which the electromagnetic wave is converged to the object, and arranging the first reflecting surface and the second reflecting surface in a detecting region,
- wherein the detecting region is determined by using a plurality of pieces of information about the relative position, and information about a time interval between a first electromagnetic wave from the first reflecting surface and a second electromagnetic wave from the second reflecting surface in a time waveform acquired by using a detection result of the detection process for the relative position corresponding to each of the plurality of pieces of information.

10. The measurement apparatus according to claim 1, wherein the detecting region is included in the collimated propagation region of the converging electromagnetic wave.

11. The measurement method according to claim 9, further comprising:
- a process of moving the relative position between the object and the convergence position of the object, the electromagnetic wave being converged at the convergence position;
- a process of acquiring the information about the time interval in the time waveform acquired by using the detection result obtained in said detecting process;
- a process of storing the information about the time interval information acquired at respective relative positions set in the moving process, and the plurality of pieces of information about the relative position corresponding to the information about the time interval; and
- a process of determining the detecting region by referring to the plurality of pieces of information stored in the storing process.

12. The measurement method according to claim 11, wherein
- in said moving process, the relative position is moved in a range in which the first reflecting surface and the second reflecting surface are located in a region extending from a collecting process region of the converging electromagnetic wave to a collimated propagation region of the converging electromagnetic wave.

13. The measurement method according to claim 9, further comprising
- a process of beforehand storing the information about the detecting region as a database, and
- a process of determining the detecting region by referring to the information of the database.

* * * * *